United States Patent
Jewell et al.

(10) Patent No.: US 10,898,583 B2
(45) Date of Patent: Jan. 26, 2021

(54) HARNESSING QUANTUM DOTS TO STUDY, VISUALIZE, AND PROMOTE IMMUNE TOLERANCE

(71) Applicants: University of Maryland, College Park, College Park, MD (US); The United States of America, as represented by the Secretary of the Navy, Washington, DC (US)

(72) Inventors: Christopher M. Jewell, Silver Spring, MD (US); Krystina Hess, Rockville, MD (US); Igor Medintz, Springfield, VA (US); Kimihiro Susumu, Alexandria, VA (US); Eunkeu Oh, Alexandria, VA (US)

(73) Assignees: University of Maryland, College Park, College Park, MD (US); The Government of the United States of America, as represented by the Secretary of the Navy, Arlington, VA (US)

( * ) Notice: Subject to any disclaimer, the term of this patent is extended or adjusted under 35 U.S.C. 154(b) by 18 days.

(21) Appl. No.: 16/093,205

(22) PCT Filed: Apr. 18, 2017

(86) PCT No.: PCT/US2017/028124
§ 371 (c)(1),
(2) Date: Oct. 12, 2018

(87) PCT Pub. No.: WO2017/184592
PCT Pub. Date: Oct. 26, 2017

(65) Prior Publication Data
US 2019/0083648 A1    Mar. 21, 2019

Related U.S. Application Data

(60) Provisional application No. 62/324,251, filed on Apr. 18, 2016.

(51) Int. Cl.
| | |
|---|---|
| *A61K 47/69* | (2017.01) |
| *A61K 39/39* | (2006.01) |
| *B82Y 10/00* | (2011.01) |
| *A61K 39/00* | (2006.01) |
| *A61P 25/00* | (2006.01) |
| *A61P 25/28* | (2006.01) |
| *A61K 9/107* | (2006.01) |
| *A61K 9/14* | (2006.01) |
| *A61K 9/51* | (2006.01) |

(52) U.S. Cl.
CPC .......... *A61K 47/6929* (2017.08); *A61K 9/107* (2013.01); *A61K 9/14* (2013.01); *A61K 9/51* (2013.01); *A61K 39/00* (2013.01); *A61K 39/39* (2013.01); *A61K 47/6923* (2017.08); *A61P 25/00* (2018.01); *A61P 25/28* (2018.01); *B82Y 10/00* (2013.01)

(58) Field of Classification Search
None
See application file for complete search history.

(56) References Cited

FOREIGN PATENT DOCUMENTS

| WO | 2009/098510 A2 | 8/2009 |
| WO | 2010/085509 A1 | 7/2010 |
| WO | 2013/072051 A1 | 5/2013 |
| WO | 2015/082656 A1 | 6/2015 |

OTHER PUBLICATIONS

Supplemental Materials for Carambia et al. "Nanoparticle-based autoantigen delivery to Treg-inducing liver sinusoidal endothelial cells enables control of autoimmunity in mice," Journal of Hepatology, Jan. 21, 2015, vol. 62, No. 6, pp. 1349-1356. (Year: 2015).*
Hess, K.L, et al., Engineering Immunological Tolerance Using Quantum Dots to Tune the Density of Self-Antigen Display, Adv. Funct. Mater., Apr. 3, 2017, vol. 27, No. 22, pp. 1-11.
Hunter, Z., et al., A Biodegradable Nanoparticle Platform for the Induction of Antigen-Specific Immune Tolerance for Treatment of Autoimmune Disease, ACS Nano, Feb. 24, 2014, vol. 8, No. 3, pp. 2148-2160.
Pires, L.R., et al., Nano- and micro-based systems for immunotolerance induction in multiple sclerosis, Human Vaccines & Immunotherapeutics, Feb. 18, 2016, vol. 12, No. 7, pp. 1886-1890.
Yeste, A., et al., Nanoparticle-mediated codelivery of myelin antigen and a tolerogenic small molecule suppresses experimental autoimmune encephalomyelitis, PNAS, Jul. 10, 2012, vol. 109, No. 28, pp. 11270-11275.

(Continued)

*Primary Examiner* — Christina Bradley
(74) *Attorney, Agent, or Firm* — Hodgson Russ LLP

(57) ABSTRACT

Provided are compositions and methods for promoting tolerance to auto-immune antigens. In general the compositions include quantum dots (QDs) that are in association with auto-immune peptide antigens. It is shown that QDs can be used to generate immunological tolerance by controlling the density of self-antigen on QDs. Peptide-QDs rapidly concentrate in draining lymph nodes, and co-localize with macrophages expressing scavenger receptors involved in tolerance. Treatment with peptide-QDs reduces disease incidence 10-fold. The degree of tolerance and the underlying expansion of regulatory T cells correlates with the density of myelin molecules presented on QDs such that higher numbers of tolerogenic particles displaying lower levels of self-peptide are more effective for inducing tolerance than fewer particles each displaying higher densities of peptide. The disclosure is therefore relevant to promoting tolerance to antigens that are involved in a variety of autoimmune disorders.

19 Claims, 18 Drawing Sheets
Specification includes a Sequence Listing.

(56) References Cited

OTHER PUBLICATIONS

Carambia, A. et al., Nanoparticle-based autoantigen delivery to Treg-inducing liver sinusoidal endothelial cells enables control of autoimmunity in mice, Journal of Hepatology, Jan. 21, 2015, vol. 62, No. 6, pp. 1349-1356.

* cited by examiner e

CL4 ligand structure

```
                              SEQUENCE LISTING

<160> NUMBER OF SEQ ID NOS: 9

<210> SEQ ID NO 1
<211> LENGTH: 21
<212> TYPE: PRT
<213> ORGANISM: Mouse

<400> SEQUENCE: 1

Met Glu Val Gly Trp Tyr Arg Ser Pro Phe Ser Arg Val Val His Leu
1               5                   10                  15

Tyr Arg Asn Gly Lys
            20

<210> SEQ ID NO 2
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 2

His His His His His Ser Ala Ala Ala Ala Ala Gly
1               5                   10

<210> SEQ ID NO 3
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 3

His His His His His Ser Ala Ala Ala Ala Ala Gly Met Glu Val Gly
1               5                   10                  15

Trp Tyr Arg Ser Pro Phe Ser Arg Val Val His Leu Tyr Arg Asn Gly
            20                  25                  30
```

Lys

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 4

His His His His His
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 5

Ala Ala Ala Ala Ala
1               5

<210> SEQ ID NO 6
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 6

His His His His His Ser Ala Ala Ala Ala Ala Gly Ile Ser Gln Ala
1               5                   10                  15

Val His Ala Ala His Ala Glu Ile Asn Glu Ala Gly Arg
            20                  25

<210> SEQ ID NO 7
<211> LENGTH: 20
<212> TYPE: DNA
<213> ORGANISM: Artificial Sequence
<220> FEATURE:
<223> OTHER INFORMATION: Synthetic adjuvant

<400> SEQUENCE: 7
tccatgacgt tcctgacgtt                                           20

<210> SEQ ID NO 8
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 8

His His His His His His
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Peptide

```
<400> SEQUENCE: 9

Ala Ala Ala Ala Ala Gly
1               5
```

HARNESSING QUANTUM DOTS TO STUDY, VISUALIZE, AND PROMOTE IMMUNE TOLERANCE

CROSS REFERENCE TO RELATED APPLICATIONS

This application claims priority to U.S. Provisional Application No. 62/324,251, filed on Apr. 18, 2016, the disclosure of which is hereby incorporated by reference.

STATEMENT REGARDING FEDERALLY SPONSORED RESEARCH

This invention was made with government support under contract no. 1351688 awarded by the National Science Foundation. The government has certain rights in the invention.

FIELD OF THE DISCLOSURE

The disclosure generally relates to methods for inducing tolerance to auto-immune antigens. More particularly the disclosure relates to use of quantum dots combined with antigens for tunable immune response modulation.

BACKGROUND OF THE DISCLOSURE

In multiple sclerosis (MS), self-reactive antibodies and T cells attack the myelin sheath insulating the central nervous system (CNS).[1, 2] Existing therapies can suppress these effects, but are not curative and leave patients immunocompromised.[3, 4] One promising strategy to overcome these hurdles is generation of regulatory T cells ($T_{REGS}$). These cells can act in a myelin-specific manner to restrain the inflammatory response against myelin without non-specific suppression.[5-7] New studies focused on more specific treatments reveal that the development of inflammation or tolerance against self-molecules is influenced by the concentration and form of antigen reaching the tissues that coordinate immune function, namely, lymph nodes (LNs) and the spleen.[5, 8-11] Thus, tunable control over the display of these self-ligands could enable more specific and effective therapies.[12] Along these lines, three recent discoveries motivated our strategy to test QDs as a nanoscale scaffold to promote tolerance. First, several reports demonstrate sub-30 nm nanoparticles drain very efficiently through lymphatic vessels and accumulate in LNs.[13, 14] Second, new studies reveal that changing the way myelin is processed and presented to the immune system can drive tolerance instead of inflammation.[15-18] For example, one group induced T cell tolerance by treatment with large microparticles decorated with myelin peptide that trafficked to macrophages expressing a scavenger receptor (MARCO) normally involved in uptake and removal of particulate debris.[15] This altered trafficking activates apoptotic clearance pathways that bias responses against these peptides toward tolerance. Lastly, two seminal papers reveal direct connections between LNs and the CNS.[19, 20] This discovery suggests engineering the response to self-antigens in LNs during T cell priming could provide a direct route to generate $T_{REGS}$ that subsequently migrate to the CNS to control pathogenic T cells (e.g., $T_H1$, $T_H17$) attacking myelin.

SUMMARY OF THE DISCLOSURE

The present disclosure relates generally to promoting tolerance to auto-immune antigens. In general the disclosure provides quantum dots (QDs) comprising peptide antigens. The disclosure in certain aspects provides a surprising discovery in that QDs having lower antigen densities, relative to QDs having higher antigen densities, showed both delayed disease onset and lower incidence in a mouse model of multiple sclerosis (MS). In particular, it is shown here for the first time that QDs can be used to generate immunological tolerance by controlling the density of self-antigen on QDs. These assemblies display dense arrangements of myelin self-peptide associated with disease in MS, and may be uniform in size (<20 nm), and can allow direct visualization in immune tissues. Peptide-QDs rapidly concentrate in draining lymph nodes, co-localizing with macrophages expressing scavenger receptors involved in tolerance. Treatment with peptide-QDs reduces disease incidence 10-fold. Strikingly, the degree of tolerance—and the underlying expansion of regulatory T cells—correlates with the density of myelin molecules presented on QDs. Thus, higher numbers of tolerogenic particles displaying lower levels of self-peptide are more effective for inducing tolerance than fewer particles each displaying higher densities of peptide. Accordingly, QDs conjugated with self-antigens provide a new platform to induce tolerance, while also permitting visualizing QD therapeutics in tolerogenic tissue domains. The disclosure is therefore relevant to promoting tolerance to antigens that are involved in a variety of autoimmune disorders.

Embodiments of the invention are demonstrated using a myelin antigen and a mouse model of MS, and thus in certain approaches the disclosure comprises one or more QDs having conjugated thereon a plurality of myelin peptide antigen molecules. In embodiments the size of the QD is from 14 to 22 nm. In embodiments, the number of myelin peptide antigen molecules on the QD are from 10 to 150, or from 15 to 65, or from 13 to 59. In one non-limiting implementation, the density of myelin peptide antigen molecules on the QD are less than or equal to 0.56 peptide antigen molecules per $nm^2$ of QD surface area.

The material used in the QDs is not particularly limited, and in one embodiment the QD comprises or is made partially or fully of CdSe/ZnS. In certain approaches, a peptide, such as a myelin antigen peptide, comprises an additional amino acid sequence that in part coordinates the peptide on the QD. In one approach a peptide antigen comprises an additional sequence comprising HHHHH-SAAAAAG (SEQ ID NO:2), wherein $(H)_5$ participates in Zn-coordination of the peptide antigen on the QD, wherein S acts as a flexible hinge to display the peptide away from the QD surface, and wherein $(A)_5$ is an alpha-helical spacer.

The disclosure includes compositions, such as pharmaceutical compositions, that can comprise any QD, and any combination of QDs, as described herein. In embodiments, QDs in a composition comprise a ratio of myelin peptide antigen to QD of from 1:1 to 150:1. In embodiments, least 80% of the QDs in the plurality have a diameter of from 10-40 nm.

In one approach the disclosure comprises promoting tolerance to an auto-antigen, such as a myelin antigen, by administering to an individual in need thereof a composition as described herein. In certain approaches, subsequent to the administration regulatory T cells ($T_{REGS}$) in the individual are expanded relative to a control. In certain embodiments, subsequent to the administration regulatory inflammatory $T_H1$ cells in the individual are not expanded, relative to a control. In some non-limiting examples, when administered to an individual, QDs comprise a lowest density of myelin peptide antigens having 17±4 myelin peptide antigens per QD, and comprise a highest density of myelin peptide antigens having 52±7 myelin peptide antigens per QD. In embodiments, a composition is administered to an individual who has a condition that comprises an autoimmune response to myelin, including but not necessarily limited to MS. In one approach the composition is administered to an individual who has MS, and subsequently one or more symptoms of the MS in the individual are alleviated or inhibited from developing. In other embodiments the individual may have Type I diabetes or another auto-immune condition, and one or more symptoms of the diabetes or the other auto-immune condition are alleviated or inhibited from developing. In certain approaches, the QDs administered to an individual comprise a ratio of myelin peptide antigen to QD of less than 150:1, and wherein alleviation or inhibition of development of the symptoms in the individual is greater than alleviation or inhibition of symptoms of the MS relative to a control value for use of QDs comprising a ratio of myelin peptide antigen to QD of 150:1 or higher. In one example, the QDs comprise a ratio of myelin peptide antigen to QD of less than 65:1, and alleviation or inhibition of development of the symptoms in the individual is greater than alleviation or inhibition of symptoms relative to a control value for administration of QDs comprising a ratio of myelin peptide antigen to QD of 65:1 or higher.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
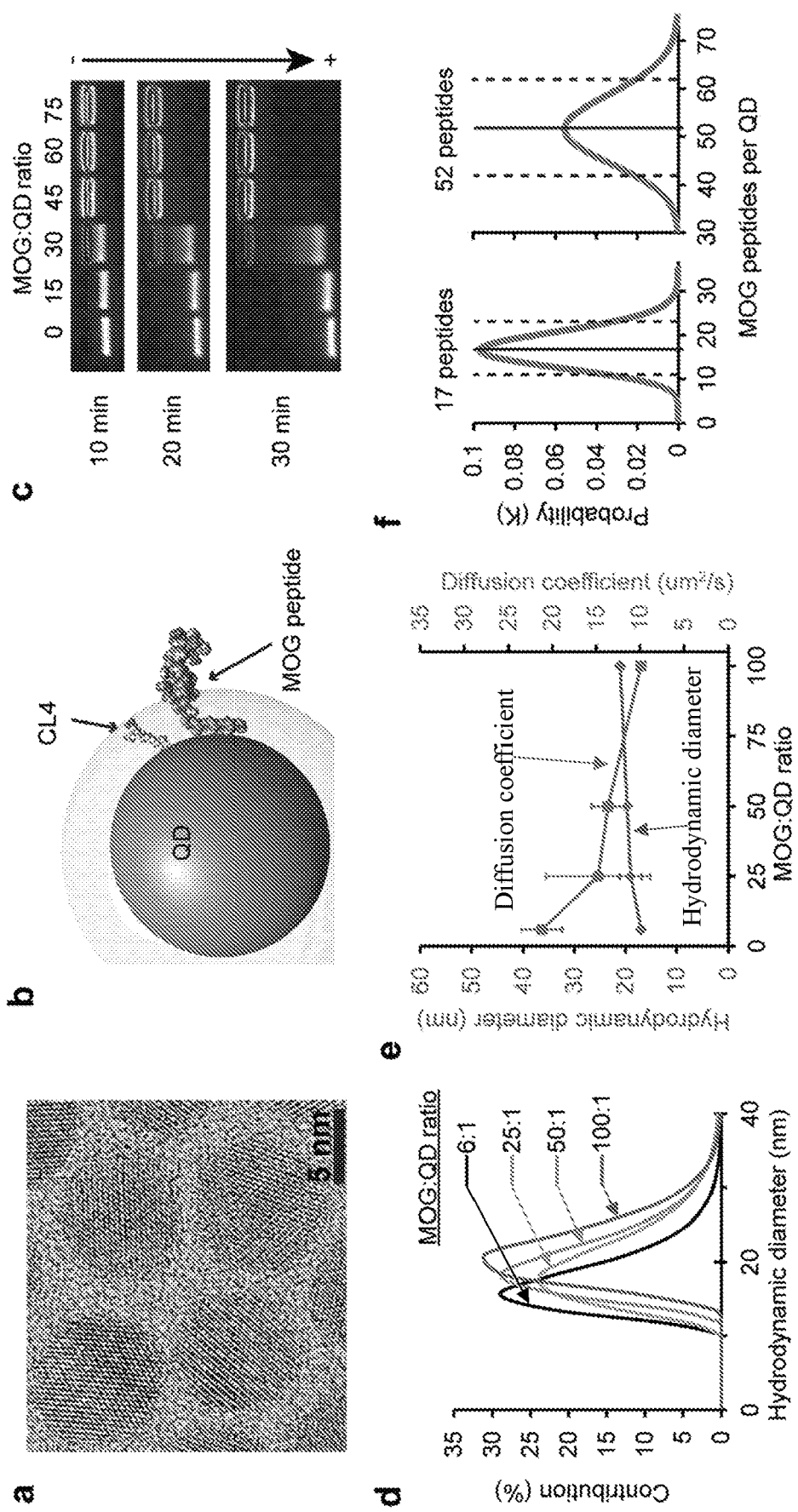
FIG. 1 shows MOG-QDs offer tunable display of MOG peptide ligands. a) TEM image of 9.2±0.8 nm CdSe/ZnS core/shell 625 emitting QDs. b) Structural simulation of the MOG-QD to scale with an energy minimized CL4 ligand attached to the surface with an extension of ~1.1 nm. c) Electrophoretic mobility of MOG-QDs was assessed in a 1% agarose gel run in 1×TBE buffer. d) MOG-QD size was measured by DLS. e) MOG-QD size was compared to rate of diffusion. f) Simulation was used to confirm MOG loading densities. Data in (e) represent mean±s.d.

Unless defined otherwise herein, all technical and scientific terms used herein have the same meaning as commonly understood by one of ordinary skill in the art to which this disclosure pertains.

Unless specified to the contrary, it is intended that every maximum numerical limitation given throughout this description includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The present disclosure is related to inducing immune tolerance in individuals who have autoimmune disorders, and is exemplified via compositions and methods that are shown to be surprisingly efficacious in reducing and even reversing symptoms of multiple sclerosis (MS) in a pertinent mouse model. In particular, the present disclosure demonstrates that quantum dots (QDs) can be harnessed to promote tolerance by designing peptide-QD displaying self-antigen at tunable densities. Notably, the extent of efficacy is demonstrated to be directly linked to the density of peptide ligands on the QD, with lower levels of self-antigen displayed on a larger number of QDs driving the most efficient tolerance. Since lymph nodes, spleens, and other immune tissues integrate local signals across the body, it is considered (without intending to be bound by any particular theory) that this finding may reflect a mechanism achieved by providing a large number of therapeutic events, even if each QD only displays a low level of the self-antigen. These outcomes, along with the antigen-specific expansion of myelin-reactive T cells in co-culture studies—and the lack of efficacy using control QDs demonstrated herein—indicate that the tolerance generated by myelin antigen-QDs is myelin-specific, and may extend broadly to other antigens.

In more detail, it is demonstrated in this disclosure that that a higher number of tolerogenic particles displaying lower levels of self-peptide is more effective for inducing tolerance than fewer particles displaying high densities of peptide. Thus, in embodiments the disclosure provides novel approaches to dose sparing.

Certain and non-limiting aspects of this disclosure are demonstrated using the well-known myelin antigen known in the art as MOG. In embodiments the disclosure demonstrates that MOG-QDs offer tunable display of MOG peptide ligands, that dendritic cells can phagocytose MOG-QDs and process and present MOG to T cells, and that MOG-QDs drain to inguinal lymph nodes (iLNs) and induce tolerance in the well-known experimental autoimmune encephalomyelitis (EAE) model. In embodiments the disclosure demonstrates expansion of regulatory T cells ($T_{REGS}$) using compositions and methods of the invention, whereas it is also shown that regulatory inflammatory $T_H1$ cells are not expanded.

With respect to the EAE mouse model, it is known in the art that it has been used to show pre-clinical efficacy for FDA approved multiple sclerosis treatments that include Copaxone, Dimethyl fumarate, Fingolimod, Interferon Beta-1A, Natalizumab, and Teriflunomide. In the current disclosure this model is used to provide evidence of the induction of tolerance to myelin antigen, supporting its use as an approach to managing MS. Furthermore, EAE is an accepted model for acute disseminated encephalomyelitis (ADEM) and acute haemorrhagic leucoencephalitis (AHLE). It is known in the art that ADEM comprises a widespread attack of inflammation in the brain and spinal cord that damages myelin, and AHLE is the severe end of the range of ADEM. Thus, the EAE model is useful for evaluating induction of tolerance to myelin antigens, such as MOG. In connection with this, in non-limiting illustrations, it is demonstrated that providing myelin antigen-QD conjugates at a fixed mass, but displaying the doses on different numbers of QDs (i.e., fixed dose of the representative myelin antigen MOG, but varying number of QDs) results in mice receiving the fewest number of peptides per QD exhibiting the lowest clinical scores in the EAE model, with scores increasing in order for increasing MOG:QD ratios tested. These differences were statistically significant at several points, including the peak of disease. Surprisingly, mice receiving the lowest MOG:QG ratio tested (25:1 MOG:QDs) exhibited a mean score 3-fold lower than mice treated with the highest ratio (65:1 MOG:QDs). Additionally, mice injected with the lowest ligand density of MOG:QDs showed both delayed disease onset and lower incidence compared with all other groups. Moreover, as is known in the art, an additional indicator of EAE severity is body weight loss. For this metric, a similar trend to that measured for clinical score was observed, where mice treated with the lowest tested MOG:QDs maintained the highest percentage of original body weight, and weight loss increased as the number of MOG peptides per QD increased.

In view of these and other results described in the examples and figures below, the disclosure provides compositions and methods for prophylaxis and/or therapy for restraining the immune response in a variety of individuals in need thereof. The disclosure includes all QD and antigen properties and methods of making and using them described herein, including but not limited to all dynamic light scattering values, all antigen and QD sizes and size dispersions, probabilities of having any particular number of antigens per QD, hydrodynamic diameters, functionalization ratios, diffusion coefficients, density of peptide ligands on QDs, ratios of QDs to antigens, antigen mass, loading levels, self-assembly properties, lymph node draining and trafficking properties, QD/antigen uptake and antigen processing values, all effects on T cells and all other components of the immune system, all effects on symptoms or other indicators of a disease condition modeled in non-human animals and which may manifest in humans, and all steps and combinations of steps. In this regard, the steps of the methods described in the various embodiments and examples disclosed herein are sufficient to carry out aspects of the present invention. Thus, in an embodiment, a method consists essentially of a combination of the steps of the methods disclosed herein. In another embodiment, a method consists of such steps. In embodiments the disclosure provides one or more provisos that the methods can exclude certain steps and/or components, such as complicating stabilizers, reactions, and/or purification steps.

The disclosure employs QDs that are in physical association with myelin antigens. It is expected that a variety of QDs can be used in embodiments of the disclosure, although some QD properties may be preferable. QDs used to demonstrate this invention were CdSe/ZnS core/shell QDs. Such QDs are known in the art and can be made using established approaches, and can be combined with peptide antigens by using and/or adapting techniques discussed herein. QDs are also commercially available. In certain examples, QDs can comprise CdS, CdTe Pb Se, PbS, PbTe, or can be silicon QDs, germanium QDs. Combinations of distinct materials and combat ions of QDs made of distinct materials can also be used. Various QD sizes can be used and have properties and myelin antigen types and values ad discussed further below.

It is expected that any myelin antigen can be used in embodiments of this disclosure, provided the myelin antigen is recognized in whole or in part by a component of the immune system of the individual in need of treatment (prior to the administration). Those skilled in the art will recognize that myelin is synthesized by different cell types, and can vary in composition and structure, but is defined as the material that makes up the so-called sheath of myelinated axons in vertebrates. Myelin in its form in myelinated axons comprises about 40% water; its dry mass is approximately 70-85% lipids and 15-30% proteins. In general, and without intending to be limited by any particular theory, it is considered that any of proteins or fragments thereof that are inappropriately recognized by the immune system of an individual in need of treatment can function as a suitable antigen in the compositions and methods of the present disclosure. In embodiments, the myelin antigen comprises a protein or immunogenic fragment thereof, exemplary proteins including but not necessarily limited to myelin basic protein (GenBank accession number NP_002376.1), myelin oligodendrocyte glycoprotein (MOG) (GenBank accession number NP_002535.3, and proteolipid protein (GenBank accession no. AAA60117.1); the amino acid sequence for each GenBank number presented in this disclosure is incorporated herein by reference as of the priority date of this application or patent. Without intending to be constrained by any particular theory, immunogenic fragments are considered to be those that are capable of being recognized by the immune system of an individual who has MS. In embodiments, the present disclosure is considered to result in induction of immune tolerance to such antigens. In embodiments, the antigen comprises or consists of myelin, a peptide fragment thereof, or a combination or peptide fragments. In certain embodiments, the composition does not comprise any surface ligand that specifically targets the composition to any cell or tissue. Based on the results presented herein, it is expected the compositions and methods of this disclosure can be adapted by those skilled in the art to address other autoimmune conditions. Thus, in embodiments, one or more peptide antigens of this disclosure can be segments of or derived from any protein-based autoantigens, including those known to be involved in the etiology of any of celiac disease, Crohn's disease, diabetes mellitus type 1, eosinophilic fasciitis, eosinophilic gastroenteritis, gastritis, Graves' disease, hypogammaglobulinemia, idiopathic inflammatory demyelinating diseases, thrombocytopenic purpura, rheumatoid arthritis, lupus erythematosus, myasthenia gravis, pernicious anemia, psoriasis, Sjögren's syndrome, and ulcerative colitis. In embodiments the peptide antigens can include but are not necessarily limited to one or more pancreatic β-cell autoantigens, or insulin B (InsB) chain autoantigens, including but not limited to $InsB_{10-18}$, or Islet-Specific Glucose-6-Phosphatase Catalytic Subunit-Related Protein (IGRP), including but not limited to $IGRP_{206-214}$, and other autoantigens, such as chromogranin A (CgA), and glutamic acid decarboxylase (GAD), GAD65, or Glial fibrillary acidic protein (GFAP), or IA-2 (islet antigen 2; tyrosine phosphatase). In embodiments the peptide antigens can be any of those described in U.S. Patent Publication No. 20120093934, from which the description and amino acid sequences of peptide antigens is incorporated herein by reference.

The QD/antigens can be provided in pharmaceutical compositions for administration by combining them with any suitable pharmaceutically acceptable carriers, excipients and/or stabilizers. Some suitable examples of pharmaceutically acceptable carriers, excipients and stabilizer can be found in *Remington: The Science and Practice of Pharmacy* (2005) 21st Edition, Philadelphia, Pa. Lippincott Williams & Wilkins. Further, any suitable delivery vehicle can be used in the invention.

Administration of formulations comprising QD/myelin antigens as described herein can be performed using any suitable route of administration, including but not limited to parenteral, intraperitoneal, intrapulmonary, oral, intra-thecal, trans or intradermal, and intra-lymph node. Parenteral infusions include intramuscular, intravenous, intraarterial, intraperitoneal, and subcutaneous administration.

In embodiments QDs of the compositions and methods of this disclosure have a diameter of from 8 nm to 40 nm. In embodiments compositions comprising a plurality of QDs and myelin antigens are provided. In embodiments, at least 80% of the QDs in the plurality have a diameter of from 8-40 nm. Thus, in embodiments the disclosure comprises a plurality of QDs or a composition comprising the QDs, wherein at least 80, 81, 82, 83, 84, 85, 86, 87, 88, 89, 90, 91, 92, 93, 94, 95, 96, 97, 98, 99, and up to 100% of the QDs have a diameter of from about 8-40 nm, inclusive, and including all ranges there between. Some non-limiting examples are provided using QDs with a diameter of 9.2±0.8 nm. In embodiments the QDs have hydrodynamic diameters ($H_D$) of from 15.0±0.24 nm to 21.0±0.63 nm. In embodiments QDs have a $H_D$ of approximately 20 nm. QD diameters can be determined with or without myelin antigens as described herein. In embodiments the QD diameter is determined when the QDs are dynamic (i.e., tumbling) and solvated. Thus, the disclosure includes QDs wherein diameters may be determined by known techniques, such as Dynamic Light Scattering (DLS). QDs can emit light at any wavelength/color known in the art for QD emissions. In non-limiting embodiments 625 nm emitting QDs are used.

The amount myelin antigen, QDs, ratios thereof, and the number of QDs such that a suitable amount of myelin antigen is administered can be determined by those skilled in the art, given the benefit of the present disclosure. In embodiments dosing takes into account that, as demonstrated herein, mice treated with the lowest ligand density of MOG:QDs showed both delayed disease onset and lower incidence compared higher densities in a model of MS.

In one embodiment, an effective amount of a composition of the invention is administered. An effective amount is an amount of the composition that stimulates an intended immune response, such and induction of tolerance, and/or a particular lymphocyte response, and/or a reduction of symptoms, and/or inhibition of progression of symptoms, and/or prevention of the development of symptoms of a condition associated with an autoimmune response directed at least in part to myelin. For QD and myelin dosing, the present disclosure includes but is not necessarily limited to antigen/QD loading of from 1-550 µg peptide/mg QD, inclusive, and including all numbers and ranges of numbers there between. In an embodiment the disclosure includes not more than 550 µg peptide/mg QD. In embodiments, the QDs and myelin antigen peptide, illustrated using MOG, can have any of the following attributes: The size of a QD having myelin peptide antigen molecules thereon is from 14 to 22 nm, and wherein the number of the myelin peptide antigen molecules on the QD are from 1 to 150, or are from 15 to 65, or are from 13 to 59. In an embodiment more than 4 myelin antigen peptides are included on a QD. In an embodiment, the density of myelin peptide antigen molecules on the QDs are less than or equal to 0.56 peptide antigen molecules per $nm^2$ of QD surface area. In embodiments, the myelin antigen comprises an additional amino acid sequence, such as HHHHHSAAAAAG (SEQ ID NO:2), wherein $(H)_5$ participates in Zn-coordination of the peptide antigen on the QD, wherein S acts as a flexible hinge to display the peptide away from the QD surface, and wherein $(A)_5$ is an alpha-helical spacer. Alternatives to the Zn-coordination segment, the flexible hinge and spacer are known in the art and can be used in embodiments of this invention. In one approach, QDs can be made biocompatible by modifying them, such as with the zwitterionic CL4 ligand, which is a small zwitterionic molecule bearing two carboxyl groups and one each secondary and tertiary amine moieties (length=~1.8 nm) and is known in the art.

In an embodiment the disclosure includes 550 µg peptide/mg QD for any antigen disclosed herein, which is a ratio of 130:1 MOG:QD. The disclosure illustrates effects of MOG:QD compositions having the following values, each of which is encompassed by the invention, as are all values and ranges of values between these non-limiting illustrations: 70 µg MOG or control (CTRL) peptide on 0.2 nanomoles QDs (a MOG/QD ratio of 100:1), or 70 µg MOG peptide on 0.2 nanomoles QDs (a MOG/QD ratio of 100:1); 14.3 µg MOG on 0.4 nanomoles QDs (a MOG/QD ratio of 17:1); 73 µg MOG on 0.2 nanomoles QDs (a MOG/QD ratio of 52:1); 70 µg MOG on 0.5 nanomoles QDs (a MOG/QD ratio of 25:1), 70 µg MOG on 0.4 nanomoles QDs (a MOG/QD ratio of 52:1), and 70 µg MOG on 0.3 nanomoles QDs (a MOG/QD ratio of 65:1). Such values can be adapted for dosing human patients, taking into account such variables as the type and stage of disease that is being treated, the overall health and medical history of the individual, the size, weight, age and gender of the individual, and other factors that will be apparent to those skilled in the art. Thus, in embodiments, the disclosure includes methods for promoting tolerance to a myelin antigen comprising administering to an individual in need thereof any of the compositions discussed above. In certain implementations, subsequent to the administration regulatory T cells ($T_{REGS}$) in the individual are expanded relative to a control. In one approach, subsequent to the administration regulatory inflammatory $T_H1$ cells in the individual are not expanded relative to a control. In certain embodiments the QDs comprise a lowest density of myelin peptide antigens having 17±4 myelin peptide antigens per QD, and wherein the QDs comprise a highest density of myelin peptide antigens having 52±7 myelin peptide antigens per QD.

In embodiments, a composition of the invention is administered to an individual in need thereof, such as an individual who has, or is at risk of developing and/or a experiencing a reoccurrence of MS, wherein the QDs comprise a ratio of myelin peptide antigen to QD of less than 150:1, and wherein alleviation or inhibition of development of the MS symptoms in the individual is greater than alleviation or inhibition of symptoms of the MS relative to a control value for administration of QDs comprising a ratio of myelin peptide antigen to QD of 150:1 or higher. In an embodiment, the QDs comprise a ratio of myelin peptide antigen to QD of less than 65:1, and alleviation or inhibition of development of the MS symptoms in the individual is greater than alleviation or inhibition of symptoms of the MS relative to a control value for administration of QDs comprising a ratio of myelin peptide antigen to QD of 65:1 or higher. Thus, the disclosure comprises tuning the ratio of myelin antigens per QD, and tuning the amount of myelin antigen as a total dose by controlling the number of QDs over which the total dose is distributed. Accordingly, to produce a desired outcome, the myelin antigen density can be adjusted so as to optimize the dose over a suitable number of QDs. Those skilled in the art will recognize that the disclosure accordingly facilitates determining the existence, severity, stage, immune status, etc. of MS or another myelin-related autoimmune condition for any particular individual and modifying the compositions of the invention to improve the presentation of the myelin antigen to that particular individual's condition, thereby providing personalized treatment approaches. Accordingly, in embodiments, the individual to whom a composition of this disclosure is administered has been diagnosed with or is suspected of having MS, and thus can include individuals who have one or a combination of primary-progressive multiple sclerosis (PPMS), relapsing-remitting MS (RRMS), secondary-progressive MS (SPMS), or progressive-relapsing MS (PRMS). In certain embodiments, the individual has been diagnosed with or is suspected of having PPMS. In this regard, and as is known in the art, PPMS is generally characterized by persistent worsening of neurologic function, but without separate relapses or periods of remission. PPMS thus differs from relapsing forms of MS in that the relapsing forms comprise at least two separate locations of damage in the central nervous system (dissemination in space) that occurred at different time points (dissemination in time). The inflammatory events that result in this damage comprise the relapses (sometimes referred to alternatively as attacks or exacerbations). In contrast, PPMS comprises a gradual change in functional abilities over time. Accordingly, because PPMS and relapsing MS are considered distinct disorders (but are not necessarily mutually exclusive in any particular individual) they have different diagnostic criteria. Specifically, PPMS can be diagnosed based on a combination of criteria that comprises a) at least one year of disease progression, which typically includes worsening of neurological function without remission, and b) at least two of: i) a type of lesion in the brain that is recognized by a medical professional skilled in the art of MS diagnosis; ii) two or more lesions of a similar type in the spinal cord; and iii) evidence in the spinal fluid of a oligoclonal band of immunoglobulins, and/or an elevated IgG index, which are both signs of immune system activity in the central nervous system. In certain embodiments of this disclosure, the individual has been diagnosed with or is suspected of having PPMS. In embodiments, PPMS may be the only type of MS that the individual is suspected of having, or has been diagnosed with.

In certain embodiments, a method of this disclosure results in a slowing of the progression of symptoms of PPMS, and can even include a reversal of PPMS progression. In connection with this and as known in the art, common symptoms of MS, which can be encompassed by PPMS, include but are not necessarily limited to fatigue, walking difficulties, spasticity, dizziness and vertigo, blurred vision and pain upon eye movement, bladder and bowel dysfunction, numbness or tingling, sexual dysfunction, pain, and cognitive changes, such as complications in the ability to learn and remember information, problem solving and the like. Less common symptoms include but are not necessarily limited to difficulties with speech or swallowing, tremors, seizures and breathing problems. In embodiments, the present disclosure comprises a method of inhibiting the progression of the severity of one or more of these or other MS symptoms in an MS patient, such as a PPMS patient. In embodiments, inhibiting or reducing a symptom means the severity of the symptom is lessened, and/or the rate at which the symptom progresses is slowed, and/or the symptom is prevented from manifesting, and/or the symptom is eliminated. To achieve any of the foregoing results, an effective amount of a composition of the invention is administered.

In embodiments, the disclosure comprises kits for prophylaxis and/or therapy for myelin-related autoimmune conditions. The kits can comprise a myelin antigen and QDs as described above, or in separate formulations for mixing together. The kits can comprise a suitable buffer and pharmaceutically acceptable excipients, carriers and the like. The components can be included in separate containers, or a single container with separate compartments. The containers can include sterile components, vials, ampules, tubes, a bolus, etc. The kits can comprise printed material, such as instructions, and/or an indication that the kit is for use in treating, for example, an MS patient.

The following examples are presented to illustrate the present disclosure. They are not intended to limiting in any matter.

Example 1

This example provides a description of peptides functionalized with self-assembling peptides.

Figure 7:
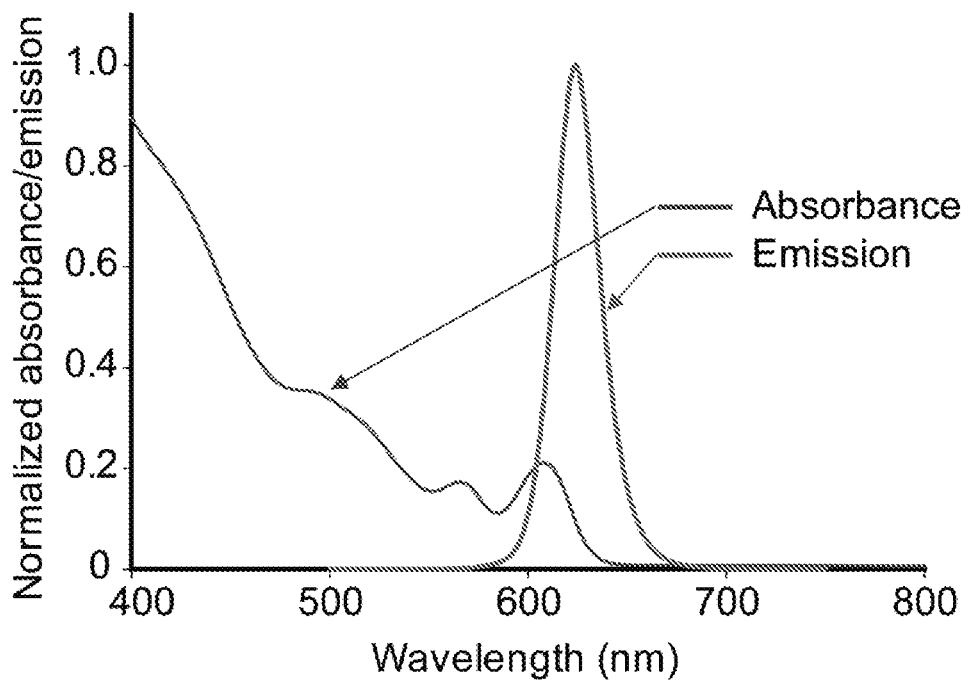
FIG. 7 shows normalized absorbance (blue) and emission (red) curves of 625 nm QDs.
Figure 8:
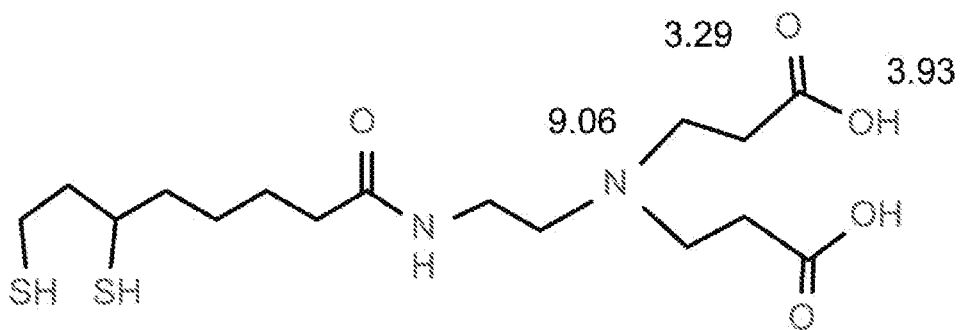
FIG. 8 shows CL4 ligand structure with estimated pKa values.

We initially analyzed 625 nm emitting CdSe/ZnS core/shell QDs (FIG. 7) with a diameter of 9.2±0.8 nm (FIG. 1a). We have previously shown this system is useful in biological contexts because these QDs can be made biocompatible using the zwitterionic CL4 ligand (FIG. 8).[27] For peptide assembly, we employed metal-affinity driven coordination to the QD surface ($K_d \sim 10^{-9}$ M), which is nearly instantaneous upon simple mixing of QDs with peptide.[25] Since this assembly follows a Poisson distribution, the actual number of peptides loaded per QD is close to the input peptide:QD ratio, except at very low densities (<4 peptides/QD). These approaches can be adapted for implementation of various embodiments of this disclosure.

Figure 9:
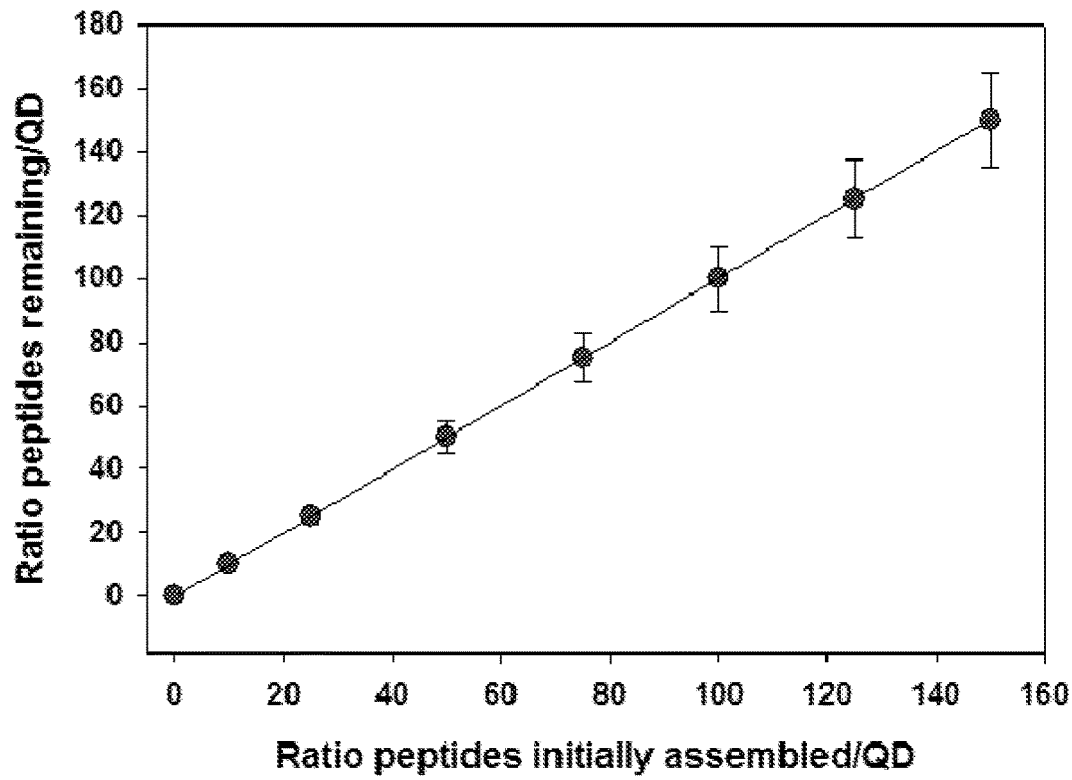
FIG. 9 shows Cy3-labeled peptide loading experiments suggest 100% loading up to 150:1 peptide:QD.

To facilitate assembly, MOG was synthesized with an N-terminus sequence of HHHHHSAAAAAG (SEQ ID NO: 2) (where the full peptide is HHHHH-SAAAAAGMEVGWYRSPFSRVVHLYRNGK, (SEQ ID NO: 3), where $(H)_5$ (SEQ ID NO: 4) participates in Zn-coordination, S acts as a flexible hinge to display the peptide away from the QD surface, and $(A)_5$ (SEQ ID NO: 5) forms a rigid alpha-helical spacer terminated by the G residue. These interactions were simulated using an energy-minimized approach, revealing the conformation in FIG. 1b. Although many conformations for the $(His)_5S(Ala)_5G$ (SEQ ID NO: 2) N-terminal portion are possible, the outcome for this segment of the full-length peptide attached to the QDs has been confirmed experimentally by Förster resonance energy transfer (FRET).[25, 26, 31-34]. With respect to the peptide attachment point on the QD surface, previous FRET studies in conjunction with modeling have confirmed that the peptides distribute around the QD surface in a random manner and do not disproportionally assemble in any given area.[35] To confirm this capability experimentally, QD modification was carried out at increasing ratios of fluorescent MOG peptide, then purified by ultracentrifugation, and quantified by fluorimetry. These studies revealed tunable modification of QDs up to a density of 150 MOG peptides per QD (FIG. 9).

Example 2

This Example demonstrates that MOG-QD exhibit uniform diameters suitable for lymphatic trafficking.

Figure 10:
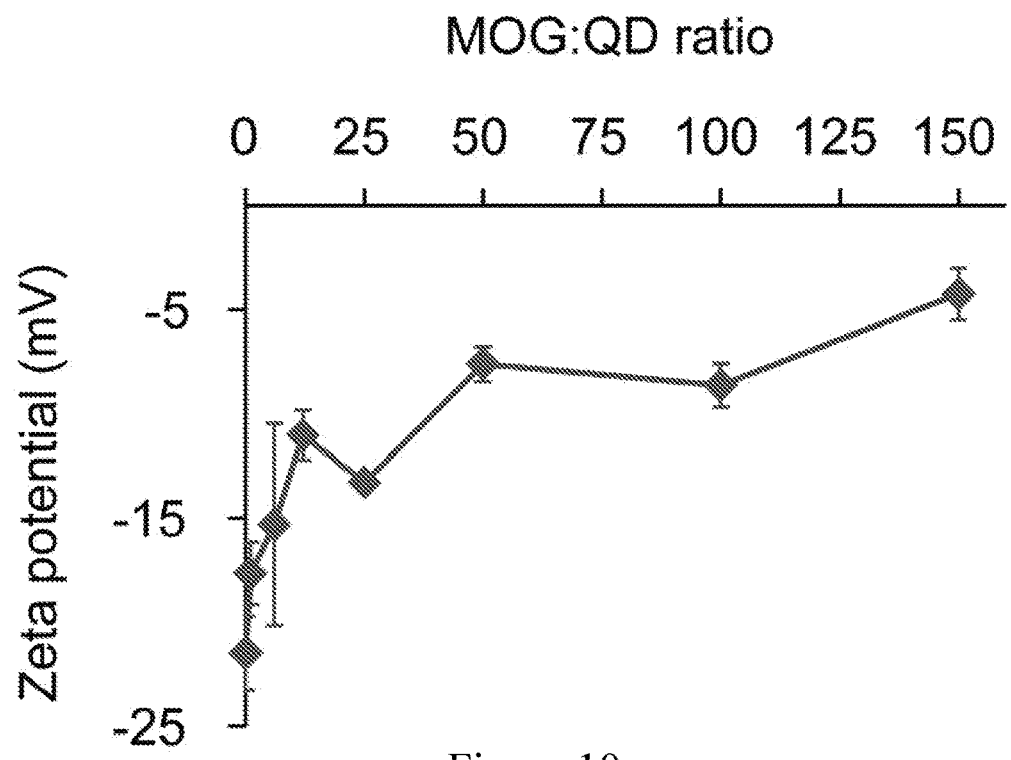
FIG. 10 shows zeta potential of MOG-QDs increases from −17.6±1.5 mV (s.d.) to −4.2±1.2 mV (s.d.) as more MOG peptide is conjugated to the QDs over a range of 1:1 to 150:1 MOG:QD.

We next characterized how different levels of modification of QDs with MOG self-antigens impacted particle size and mobility. Electrophoretic mobility in agarose gels confirmed an inverse relationship between the MOG:QD conjugation ratio and migration (FIG. 1c). Since MOG peptide has a net charge of +4, the observed patterns are consistent with a less negative charge as the MOG:QD ratio increases until charge balance is approached and migration stops. These effects were further confirmed with zeta potential measurements that revealed less negative charges as a function of increasing MOG:QD ratios (FIG. 10). Dynamic light scattering (DLS) indicated MOG-QD conjugates were monodisperse (FIG. 1d), with control over MOG conjugation to QDs further shown by hydrodynamic diameters ($H_D$) increasing from 15.0±0.24 nm to 21.0±0.63 nm over MOG:QD functionalization ratios of 1:1 to 100:1 (FIG. 1e, blue, as indicated). The diffusion coefficient decreased correspondingly over this same set of ratios (FIG. 1e, red, as indicated). MOG-QDs prepared at ratios up to 100:1 exhibited $H_D$ of approximately 20 nm, optimal for drainage to LNs.[13, 14] Thus, within an immunologically-relevant size range, QDs with a variety of ligands densities could be generated. In particular, in the cell and animal studies below, a range of 17:1 to 65:1 MOG:QD ratios were used. Experimental measurements of the density of peptide ligands displayed on the QDs (FIG. 9) were also in good agreement with simulations of peptide-QD assembly for ratios of 17:1 and 65:1, corresponding to conjugates with 17±4 peptides and 52±7 peptides assembled per QD (FIG. 1f).

While recent studies aimed at inducing tolerance have used microparticles or larger nanoparticles (~100-500 nm),[7, 15, 16] the results above highlight unique features of QDs, including 5-50 fold smaller diameters (<20 nm) for efficient concentration in LNs. This size range is noteworthy in the context of lymphatic drainage. It has been previously shown that even particles on the size range of 100 nm drain inefficiently to LNs, while a diameter of 20 nm dramatically improves lymphatic trafficking.[14] Further, MOG-QD particles also self-assemble, allowing facile administration without need for complicating stabilizers, reactions, or purification steps. With respect to loading, in contrast to the typical loading levels of several or tens of micrograms of peptide per milligram of nanoparticle carrier, the MOG-QDs of this disclosure offer loading as high as 550 µg peptide/mg QD for 130:1 MOG:QD, as well as direct tuning of surface display density. Using QDs as shuttles for self-peptides also may allow for visualization and tracking of therapeutic conjugates without photobleaching, additional probes, or dissociation of dyes from a carrier.

Figure 2:
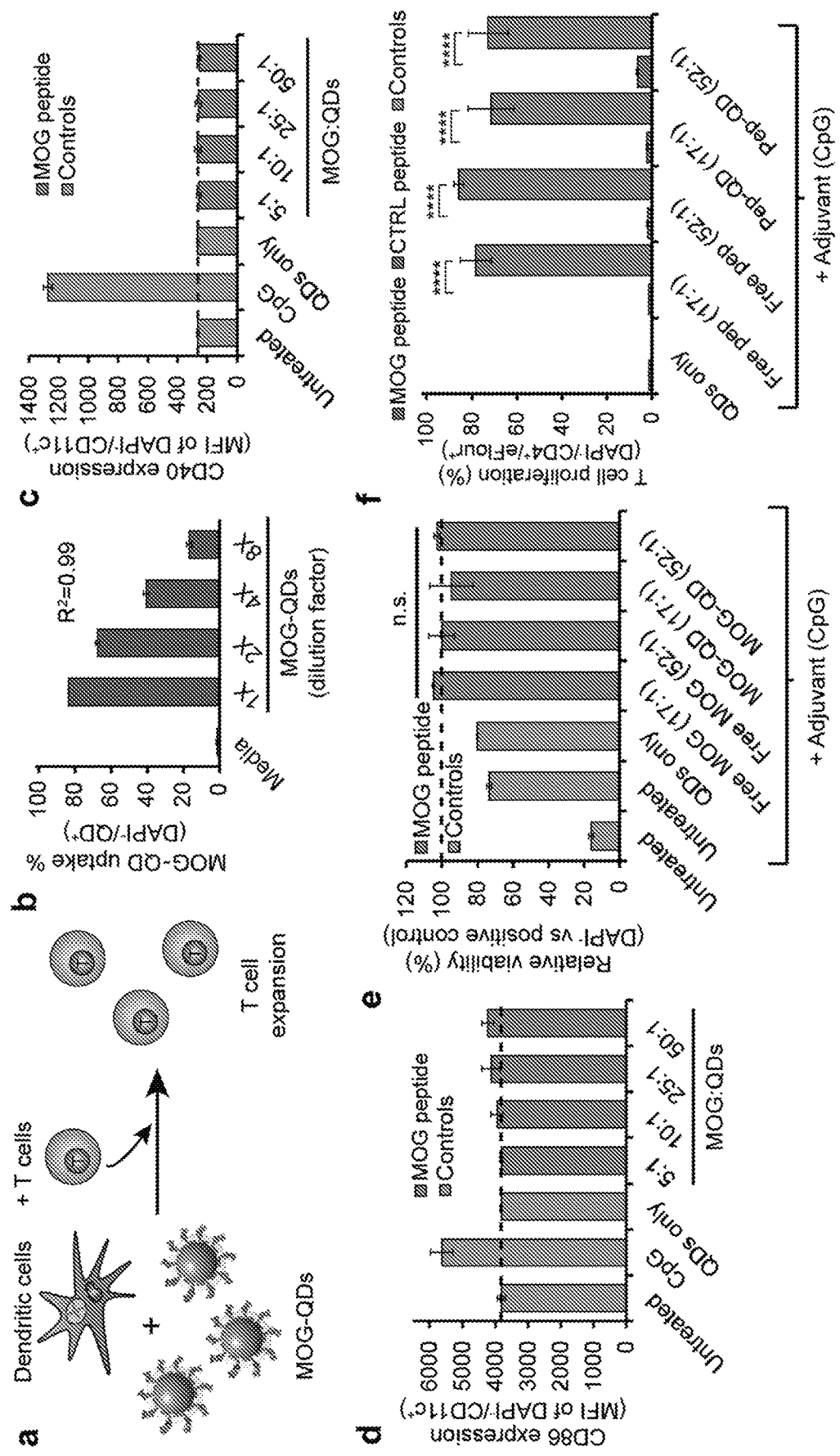
FIG. 2 shows DCs can phagocytose MOG-QDs and process and present MOG to T cells. a) DCs were incubated with MOG-QDs and transgenic 2D2 T cells that proliferate in response to MOG. b) DC uptake of MOG-QDs was quantified by fluorescent intensity by flow cytometry. DC activation was measured by expression of CD40 (c) and CD86 (three bars on the left are controls, 4 bars on the right are MOG peptide) (d) activation markers (three bars on the left are controls, 4 bars on the right are MOG peptide). e) Viability was assessed by DAPI staining 72 hours after cell treatment (three bars on the left are controls, 4 bars on the right are MOG peptide). f) 2D2 T cell proliferation was quantified by proliferation dye dilution by flow cytometry (two left bars are controls, for each data set following, the left bar is CTRL peptide and the right bar is MOG peptide). Data in (b)-(f) represent the mean (N=3)±s.d. Statistical significance was determined by one-way ANOVA with p values ≤0.05 considered significant (****$p<0.0001$; ns=not significant).
Figure 11:
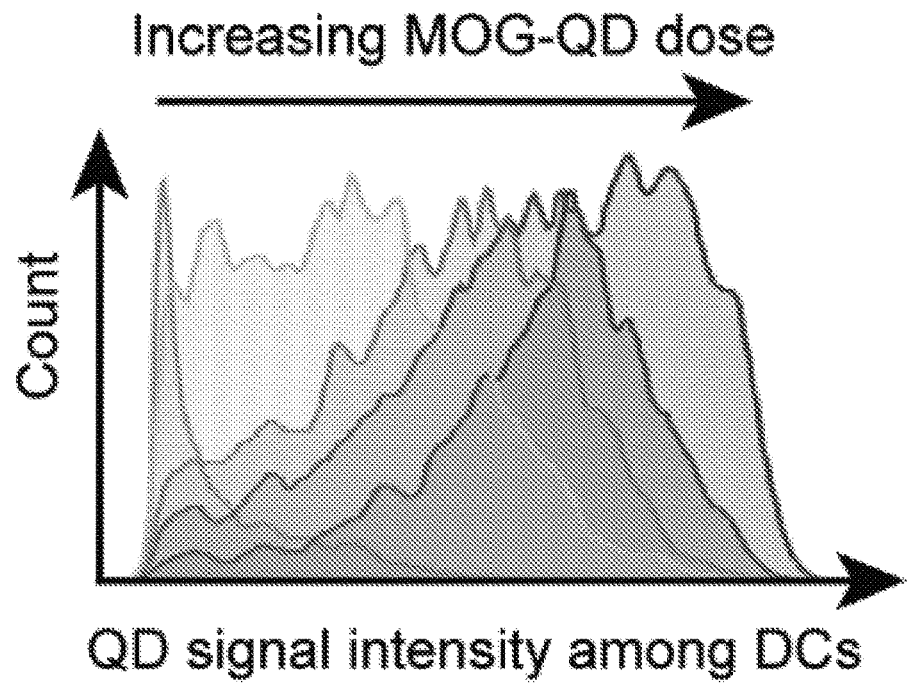
FIG. 11 shows size distribution of 150:1 MOG:QDs measured by DLS.
Figure 12:
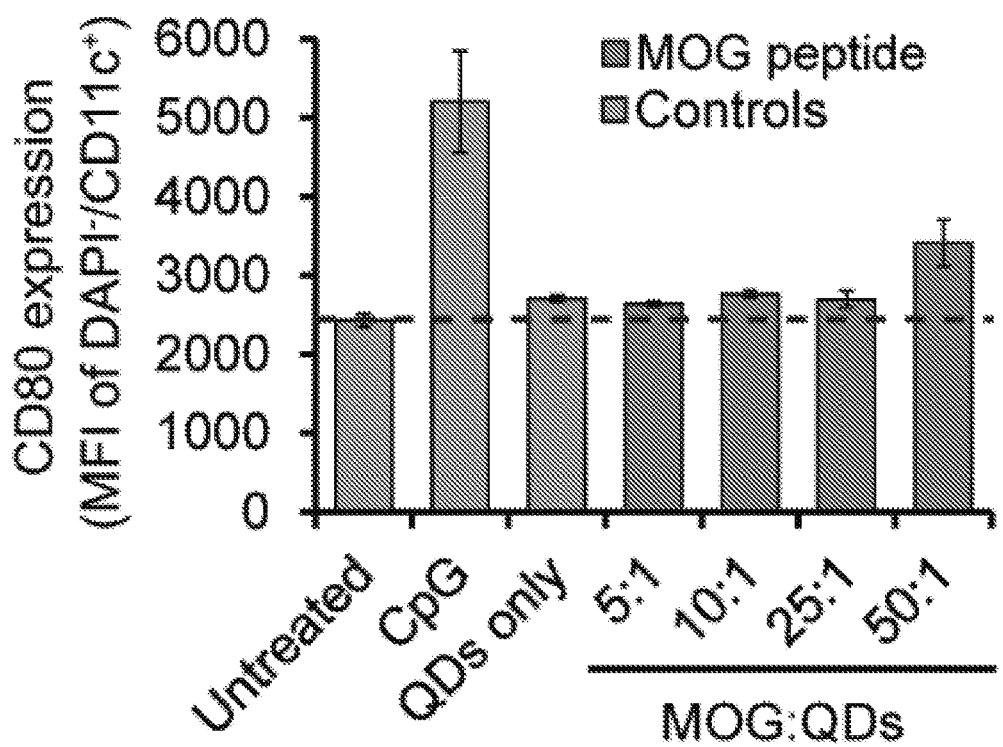
FIG. 12 shows representative histograms demonstrating DC uptake of MOG-QDs.
Figure 13:
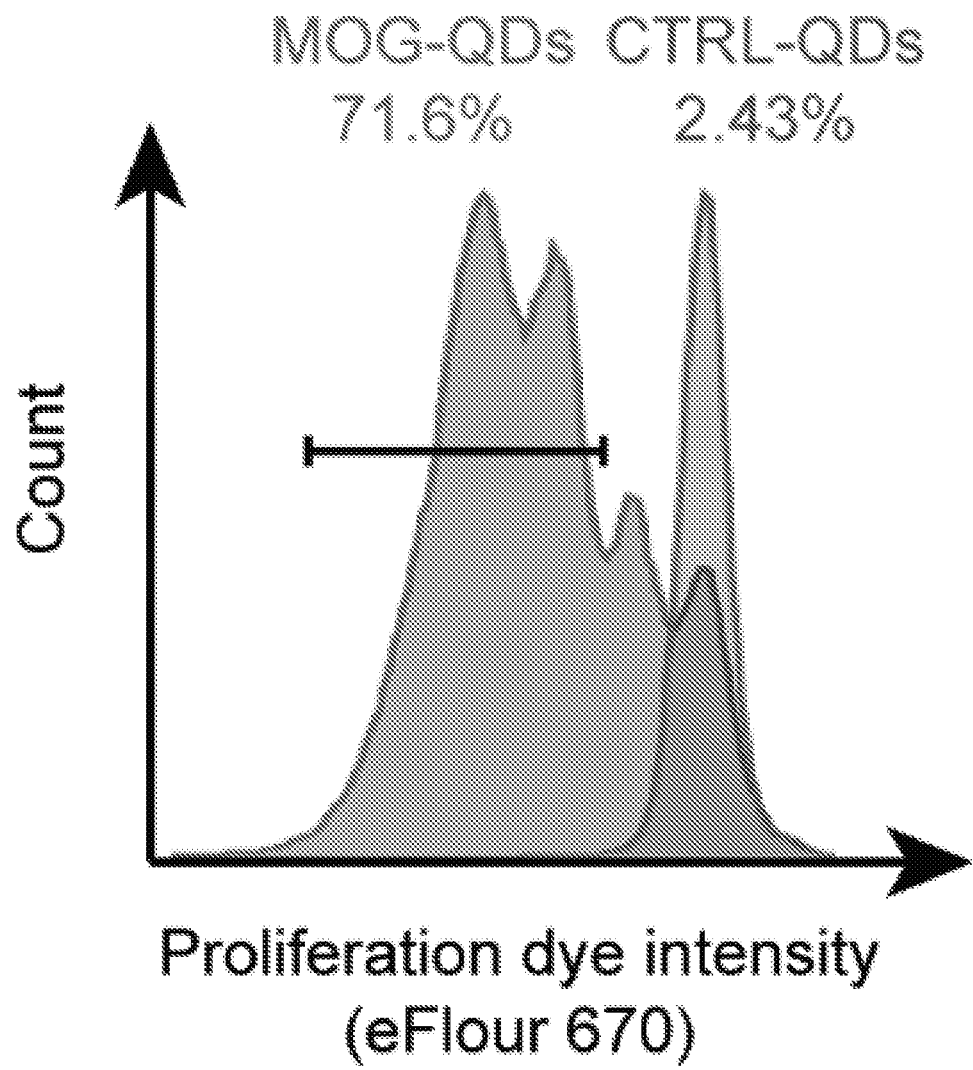
FIG. 13 shows DC activation was measured by expression of CD80 activation marker.

To evaluate the unique features of QDs for modulating immunity, we first tested uptake and antigen processing of MOG-QDs using conjugates at the highest antigen density we characterized, 150:1 (FIG. 10, FIG. 11). Dendritic cells (DCs) isolated from mouse spleens were incubated with MOG-QDs or co-cultured with MOG-QDs and transgenic T cells recognizing MOG when displayed by DCs (FIG. 2a). Flow cytometry analysis of DC cultures revealed efficient, dose-dependent uptake of QDs (FIG. 2b, FIG. 12), but these conjugates—lacking inflammatory signals—did not activate DCs, as indicated by the expression levels of CD40 (FIG. 2c), CD86 (FIG. 2d), and CD80 (FIG. 13). This finding is notable because many common polymeric carriers (e.g., poly(lactide-co-glycolide) exhibit intrinsic features—such as charge or repetitive monomers—that can activate innate immune pathways and cause inflammation.[36] These outcomes could worsen disease in the context of autoimmunity.

Figure 14:
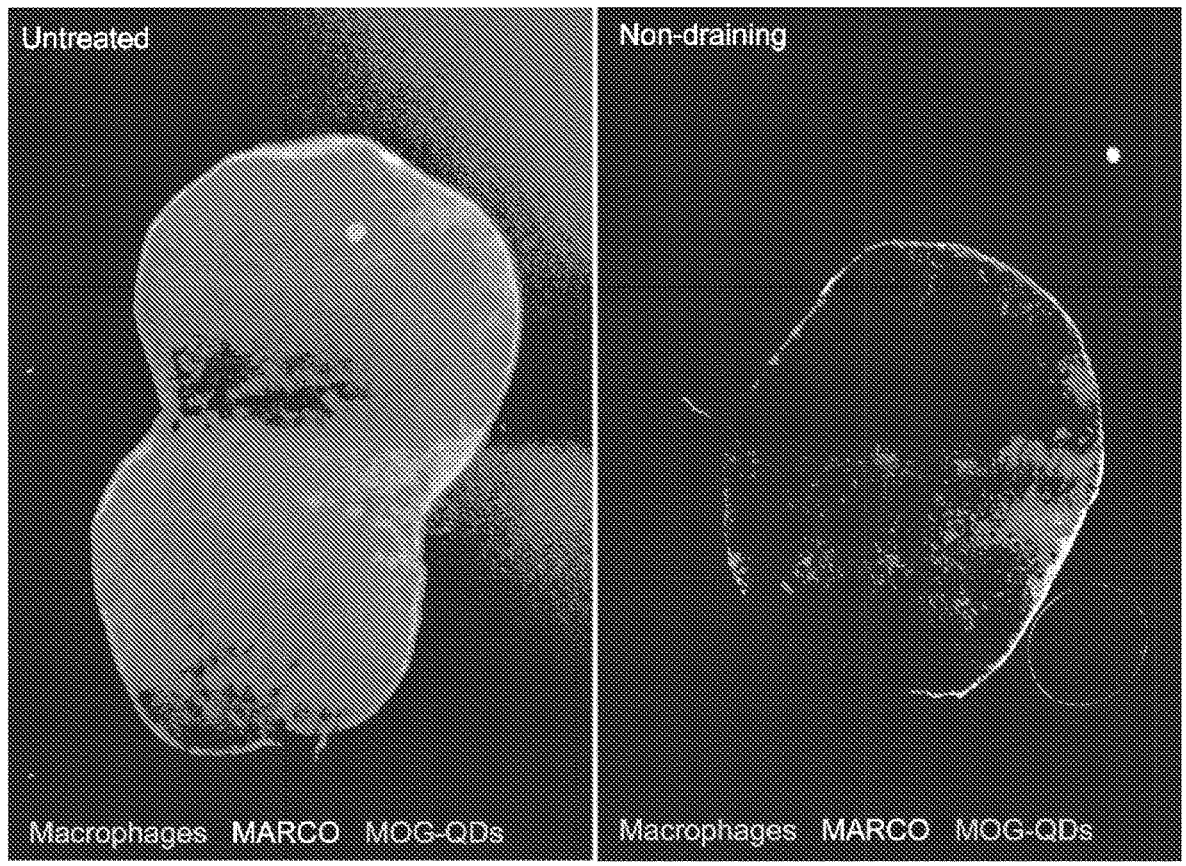
FIG. 14 shows histograms showing proliferation dye dilution representing generations of T cell proliferation in response to antigen recognition.

We next tested if MOG displayed on QDs is processed and presented in a manner that is accessible to myelin-reactive CD4$^+$ T cells from 2D2 transgenic mice. When 2D2 T cells encounter MOG presented by DCs with the correct co-stimulatory signals, these cells proliferate. In these approaches, DCs were incubated with a fixed number of QDs, but displaying different densities—either 17 or 52 peptides per QD—of MOG ligand or an irrelevant peptide ligand from ovalbumin (CTRL). To drive co-stimulatory signaling, DCs were also treated with a common molecular adjuvant (CpG). DAPI staining was used to evaluate the effect of MOG-QD treatment on cell viability in co-cultures relative to treatment with free MOG (FIG. 2e). This DNA binding stain enters leaky (i.e., damages) cell membranes more efficiently than cells with intact membranes. Thus FIG. 2e suggested MOG-QDs did not cause toxicity by this measure. During T cell co-culture, MOG-QDs caused high levels of proliferation, indicated by a dramatic dilution of signal from a fluorescence reporter as successive generations of T cells divided (FIG. 2f, FIG. 14). These levels were equivalent to values measured for free MOG, while neither CTRL-QDs nor free CTRL peptide caused proliferation (FIG. 2f). This result demonstrates that conjugation of MOG to QDs does not interfere with the ability of DCs to process and present peptides, and that these materials can support antigen-specific T cell proliferation. In mice and humans, naïve MOG-specific CD4$^+$ T cells have the capacity to develop into either inflammatory phenotypes (e.g., $T_H1$, $T_H17$) or $T_{REGS}$, depending on the form of antigen presentation (e.g., soluble vs. particulate) and the other signals encountered during T cell differentiation.[3, 5, 9] Thus, we next employed a common mouse model of MS to test if MOG-QDs traffic to tolerogenic domains of lymph nodes and polarize T cells to promote tolerance as a function of the density of ligands displayed.

Example 3

Figure 3:
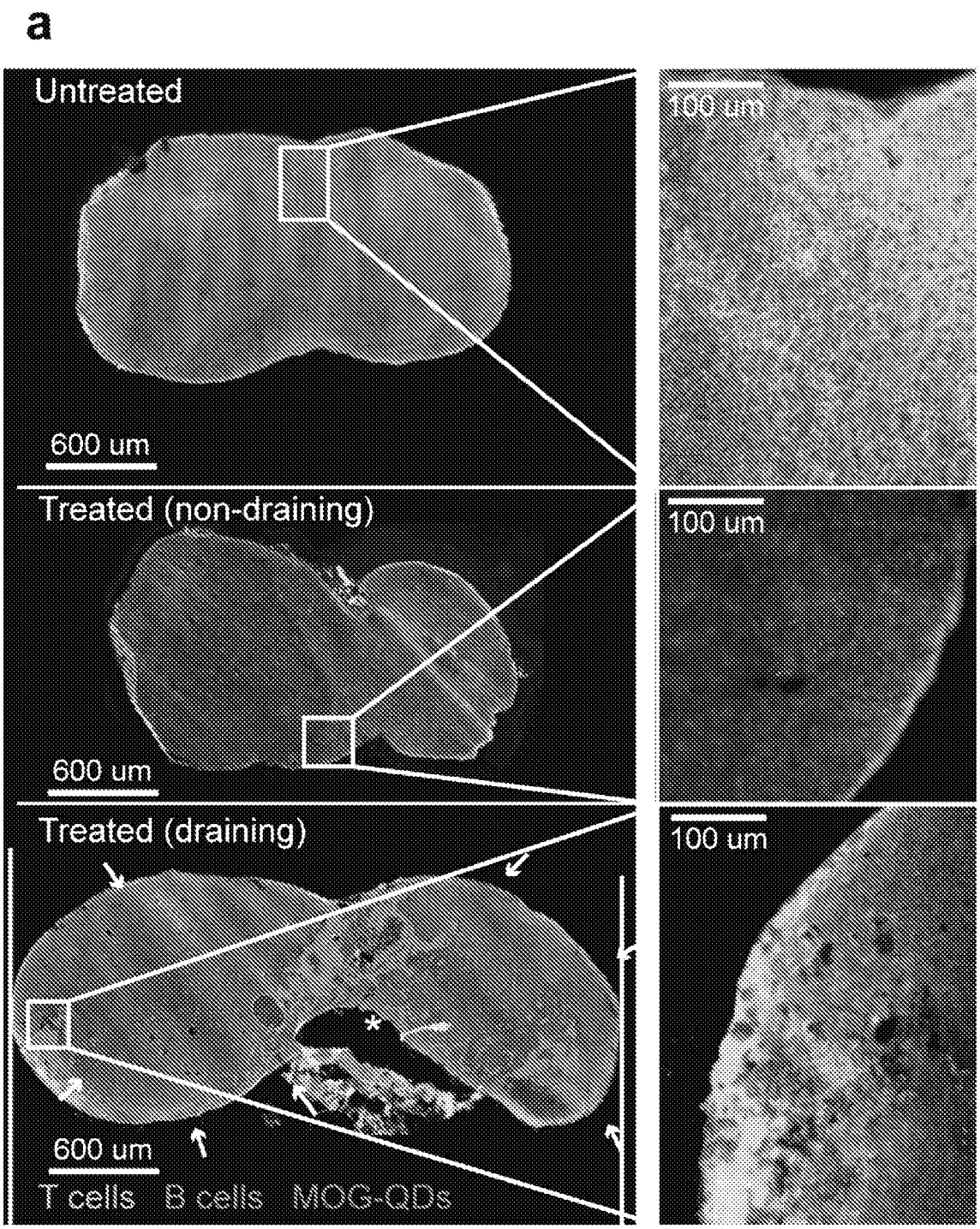
FIG. 3 shows MOG-QDs drain to the iLN and induce tolerance in EAE. a) iLNs were removed 24 hours after MOG-QD injection, stained for T and B cells, and visualized by fluorescent microscopy. MOG-QD signal in iLNs was quantified by flow cytometry (b) and (c). d) Viability of the LNs following MOG-QD injection was assessed by DAPI staining. e) iLN sections from this study were additionally stained for macrophage markers and the scavenger receptor MARCO. Data in (c) and (d) represent samples (N=3)±s.d., with statistical significance determined by one-way ANOVA with post-test corrections for multiple comparisons. P values ≤0.05 were considered significant (****$p<0.0001$; ns=not significant).
Figure 3:
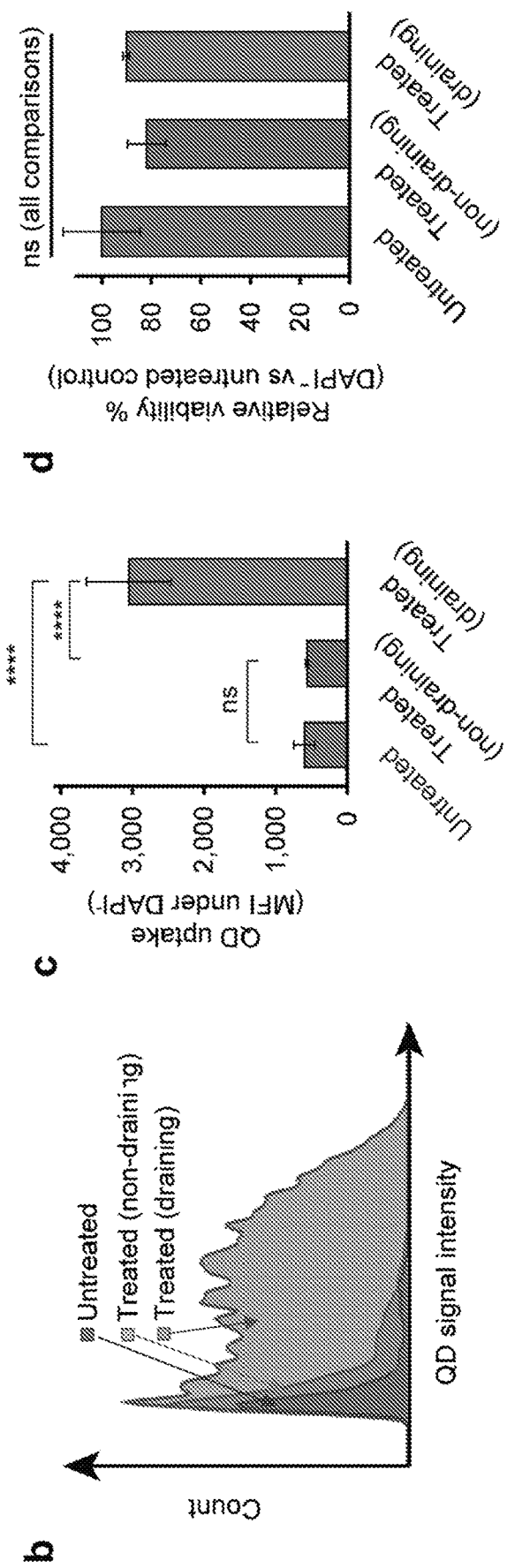
Figure 3:
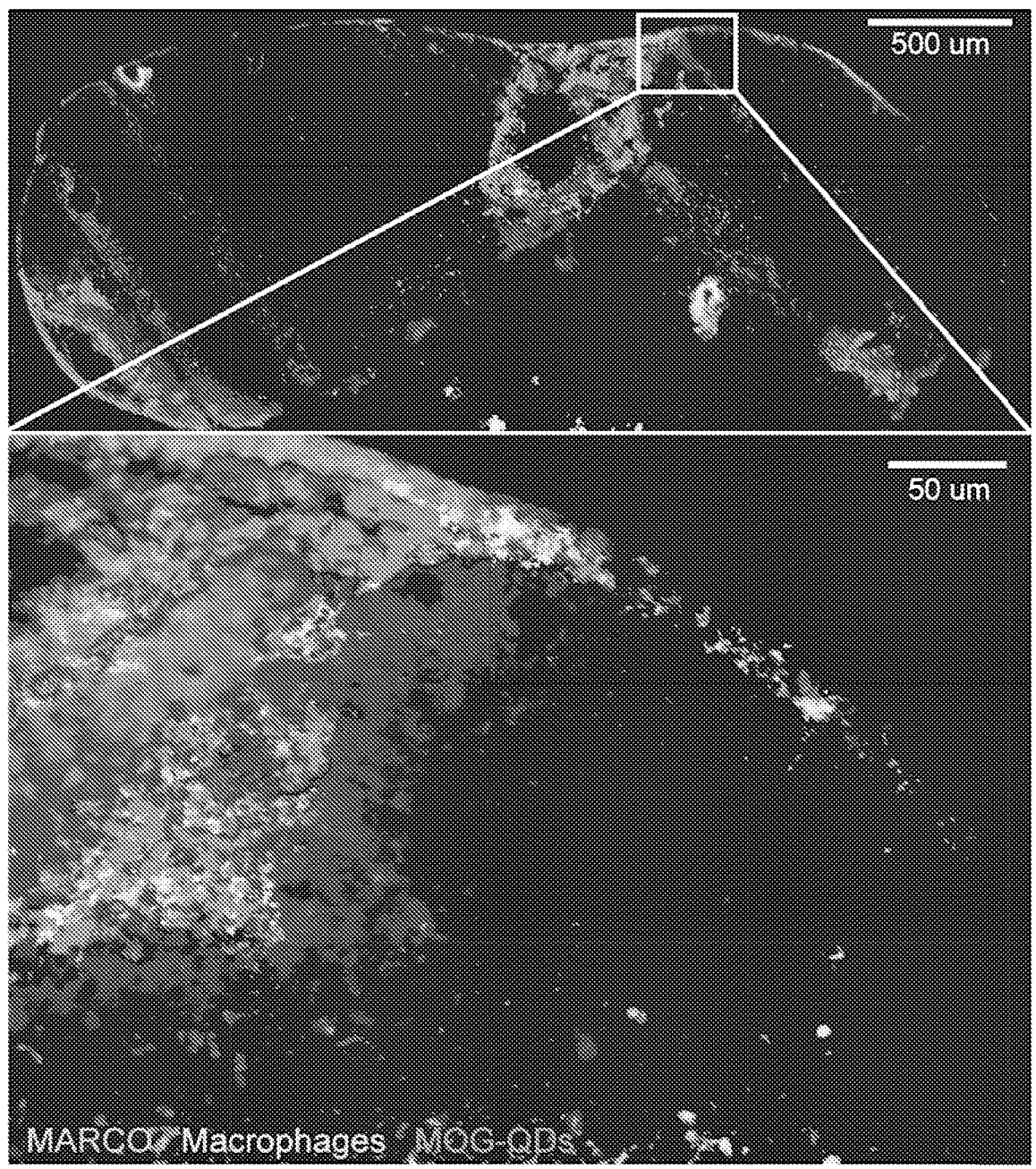

This Example provides a description of draining Lymph node imaging and analysis. This was begun by administering MOG-QDs to C57BL/6 mice by subcutaneous (s.c.) injection, then by use of fluorescence microscopy to assess lymphatic drainage. After 24 hours the draining and non-draining inguinal LNs (iLNs) were harvested, sectioned, and stained for common lymphocytes (B cells, B220; T cells, CD3). The draining iLN from injected mice exhibited striking levels of MOG-QDs in the medullary sinus (asterisk) and subcapsular sinuses (arrows), as well as less concentrated, widespread distribution in the T cell zone/paracortex (FIG. 3a). The non-draining iLN showed a miniscule, but detectable, level of MOG-QD fluorescence, while signal was absent in iLNs from untreated mice (FIG. 3a). Flow cytometry confirmed these results, revealing high levels of MOG-QDs only in the draining iLNs (FIG. 3b,c). Further, there was no difference in DAPI staining levels in the cells of tissues containing MOG-QDs compared to LNs of untreated mice (FIG. 3d).

Figure 15:
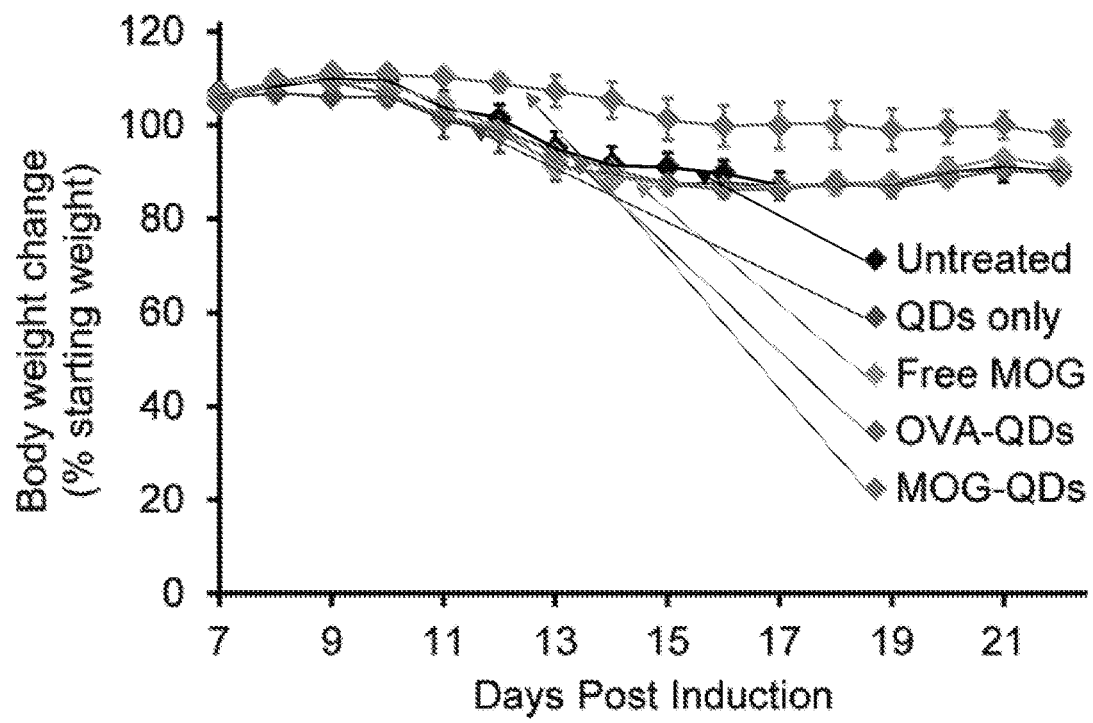
FIG. 15 shows an untreated iLN shows positive staining for macrophages and minimally, the scavenger receptor MARCO. The non-draining iLN of a mouse treated with MOG-QDs shows a small amount of MOG-QD fluorescence that is colocalized with macrophages and MARCO.

To determine if MOG-QDs might traffic to marginal zone macrophages and tolerance-inducing scavenger receptors, we stained iLNs for F4/80 and MARCO, respectively. MOG-QDs were frequently co-localized with both macrophages and MARCO throughout the iLN (FIG. 3e). This co-localization was also observed among the low levels of QDs in non-draining iLN, while QD signal was absent in control iLNs from untreated mice (FIG. 15). These experiments support the concept that altering the trafficking of self-antigen can promote tolerance by directing self-peptides to tissues and pathways (e.g., MARCO) already primed to generate regulatory responses, instead of inflammatory responses. Studies with large polymer nanoparticle or microparticles conjugated with self-antigen reveal this conjugation leads to trafficking to macrophages expressing MARCO.[15-17] This discovery is supported by natural immune mechanisms that direct fragments from apoptotic cells to particular regulatory microdomains in LNs that help maintain tolerance against self-cells (e.g. recycling red blood cells).[37] Our findings demonstrate that MOG-QDs drain very efficiently through lymphatics, allowing direct visualization of co-localization with macrophages and scavenger receptors involved in apoptotic clearance and promotion of tolerance against antigens reaching these domains.[38]

Example 4

Figure 4:
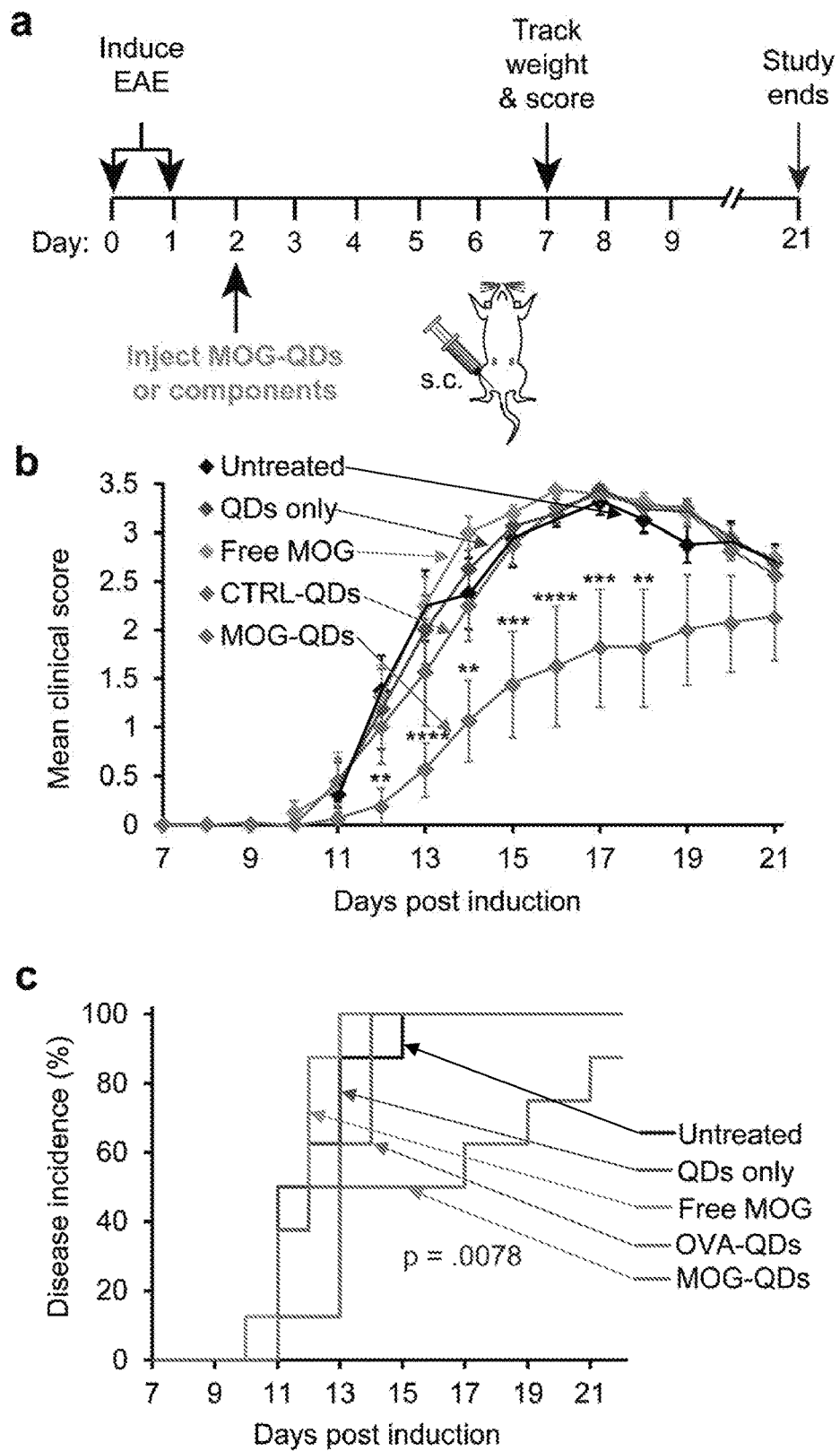
FIG. 4 shows a) mice were induced with EAE on days 0 and 1 and injected with MOG-QDs or component controls on day 2. b) Disease progression was monitored by clinical score through day 21. c) Disease onset was defined as the first day a mouse displayed symptoms. Incidence was tracked through day 21. Data in (b) represent samples (N=8)±s.e.m. p values ≤0.05 were considered significant ($p<0.01$, *$p<0.001$, ****$p<0.0001$).
Figure 16:
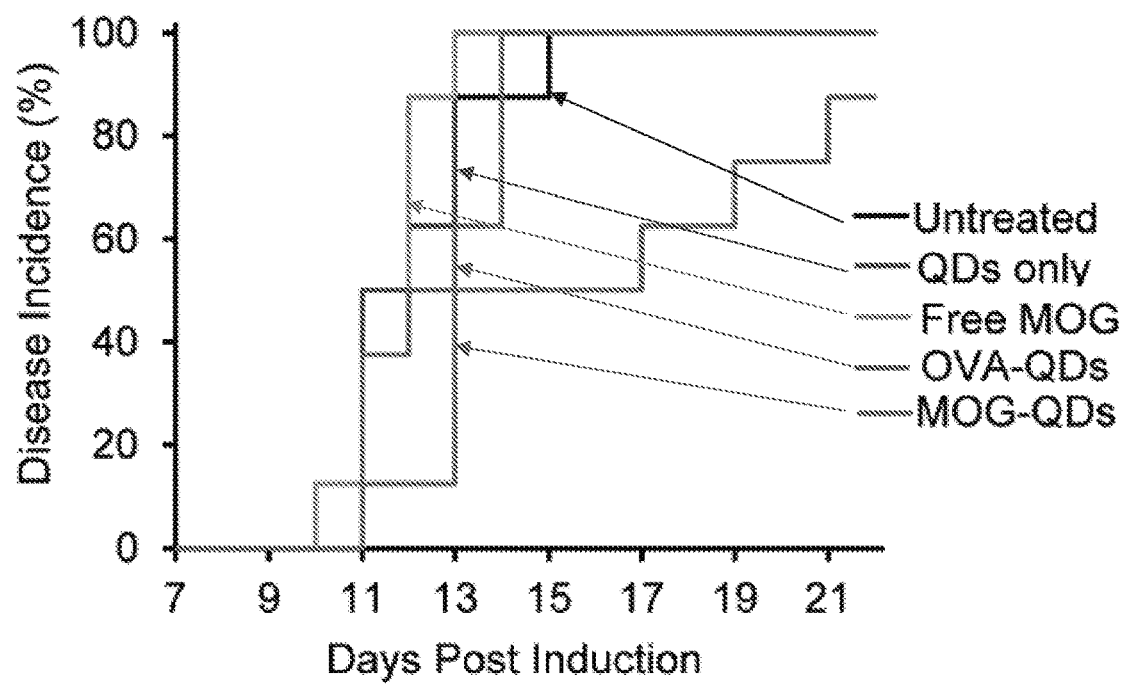
FIG. 16 shows body weight change was measured daily as an indicator of disease severity for mice receiving MOG-QDs or control treatments.

This Example demonstrates that MOG-QDs improve EAE, while QDs or MOG alone, or CTRL-QDs do not. We first induced mice with experimental autoimmune encephalomyelitis (EAE), a myelin-driven model of MS that results in loss of motor function and development of total paralysis over 2-3 weeks.[6, 7, 39] Two days later, mice received a single s.c. injection of MOG-QDs or one of several control treatments: free MOG, CTRL-QDs, or QDs only (FIG. 4a). The groups were then monitored daily for both paralysis and weight loss, a common symptom of disease. Paralysis was measured using a standard clinical disease scoring rubric in which increased clinical score corresponds to more severe paralysis. Compared with untreated mice and control groups receiving QDs only, free MOG, or CTRL-QDs, the MOG-QDs conferred a striking therapeutic effect on both disease progression (FIG. 4b) and weight loss (FIG. 16). For clarity, statistics are only shown comparing MOG-QDs against the untreated control group. Regardless of time point, however, none of the groups except MOG-QDs caused significant differences in clinical scores when comparing treatments. Mice treated with MOG-QDs also exhibited substantially decreased disease incidence (FIG. 4c). Further, there were no differences in disease incidence between untreated mice and those receiving the other treatments. Importantly, the lack of efficacy with the CTRL-QDs suggests MOG-QDs promote tolerance in a myelin-dependent manner. With clear indications of the role of each component, we next tested how the density of peptide displayed by QDs impacted T cell function, tolerance, and therapeutic effect.

Example 5

Figure 5:
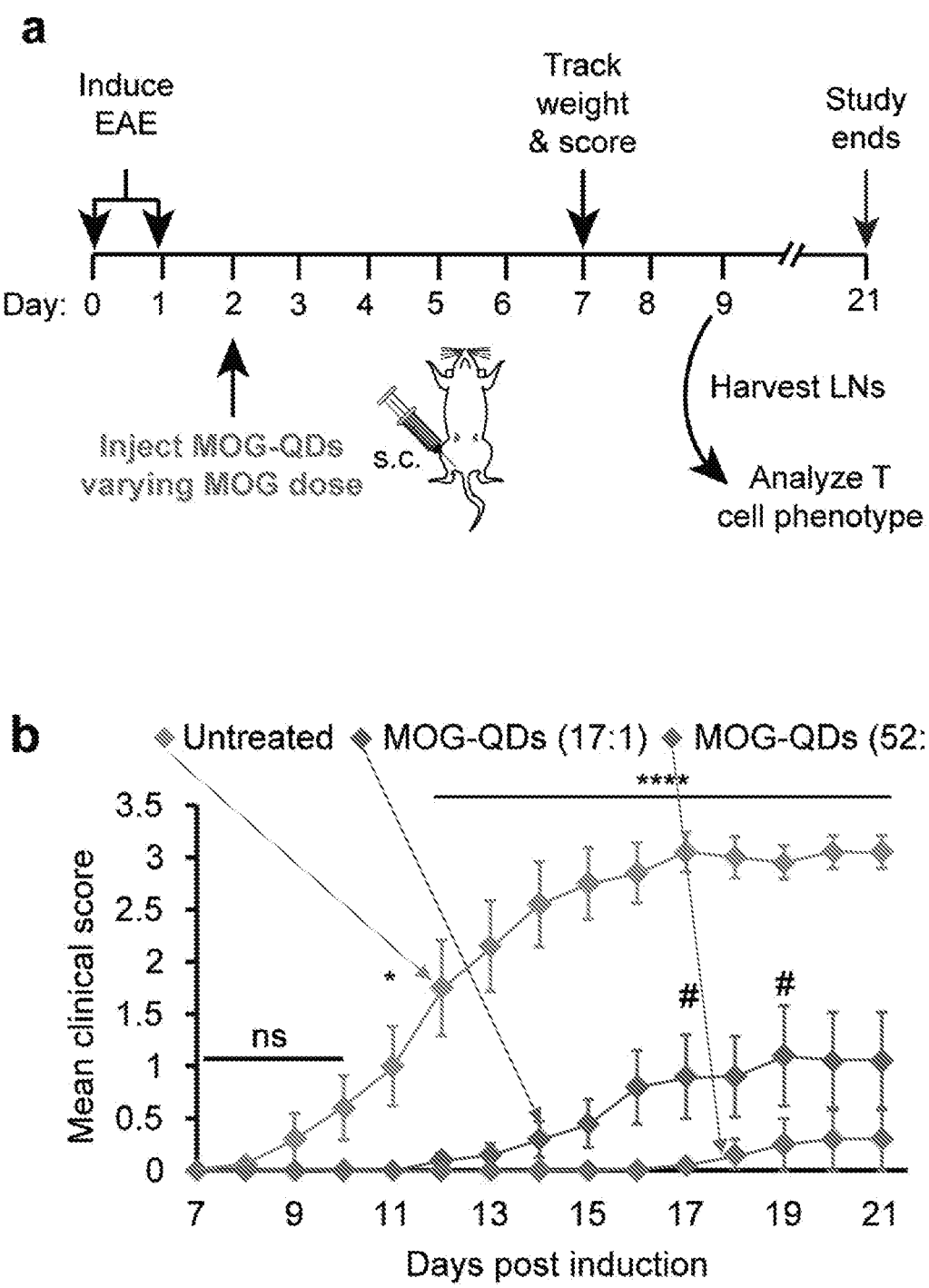
FIG. 5 shows MOG-QD treatment expands $T_{REGS}$ and increased MOG dose enhances tolerance. Mice were induced with EAE and treated with MOG-QDs (17:1 or 52:1) (a). Mice were monitored daily using a standard clinical EAE scoring rubric (b), where disease onset is the first day that symptoms arise (c). At peak disease (day 17), mean score was compared between groups (d). In a separate similar experiment, the iLNs of mice were harvested to stain for $T_{REGS}$ (e) and (f) and the $T_{H}1$ phenotype (g). Data in b, c, and d represent the mean (N=10)±s.e.m. Data in f and g represent the mean (N=5)±s.d. Statistical significance for b was determined by two-way ANOVA with post-test corrections for multiple comparisons. For day 21 in c, and d, f, and g, one-way ANOVA with post-test corrections for multiple comparisons was used. Log-rank tests were used in analysis of disease incidence in c. For all tests, p values ≤0.05 were considered significant (*$p<0.05$, $p<0.01$, **$p<0.0001$; ns=not significant). In b, all asterisks indicate statistical significance for comparisons of either MOG-QD treatment group against untreated mice. #indicates significance of $p<0.05$ for comparisons of MOG-QD (17:1) against MOG-QD (52:1).
Figure 5:
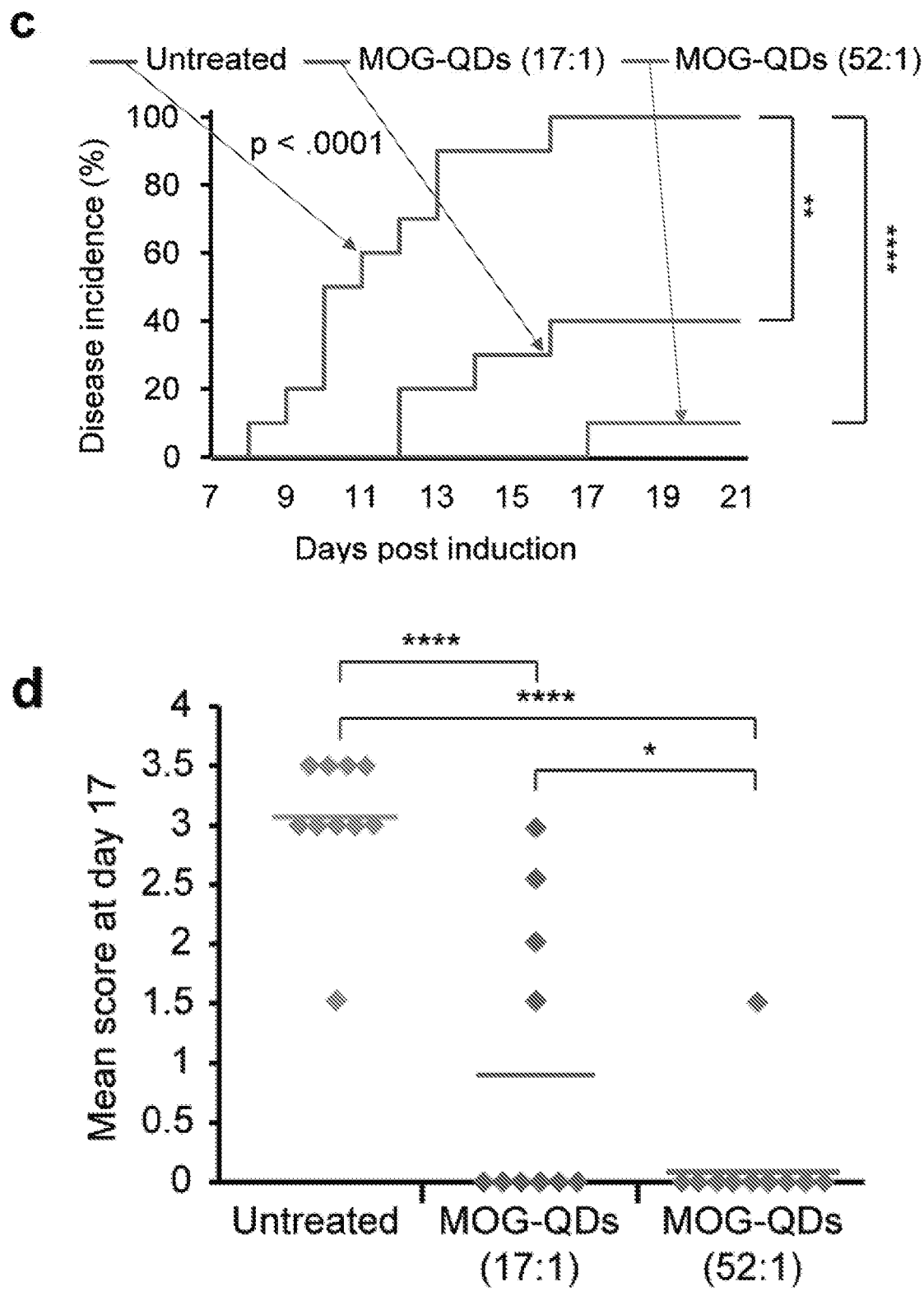
Figure 5:
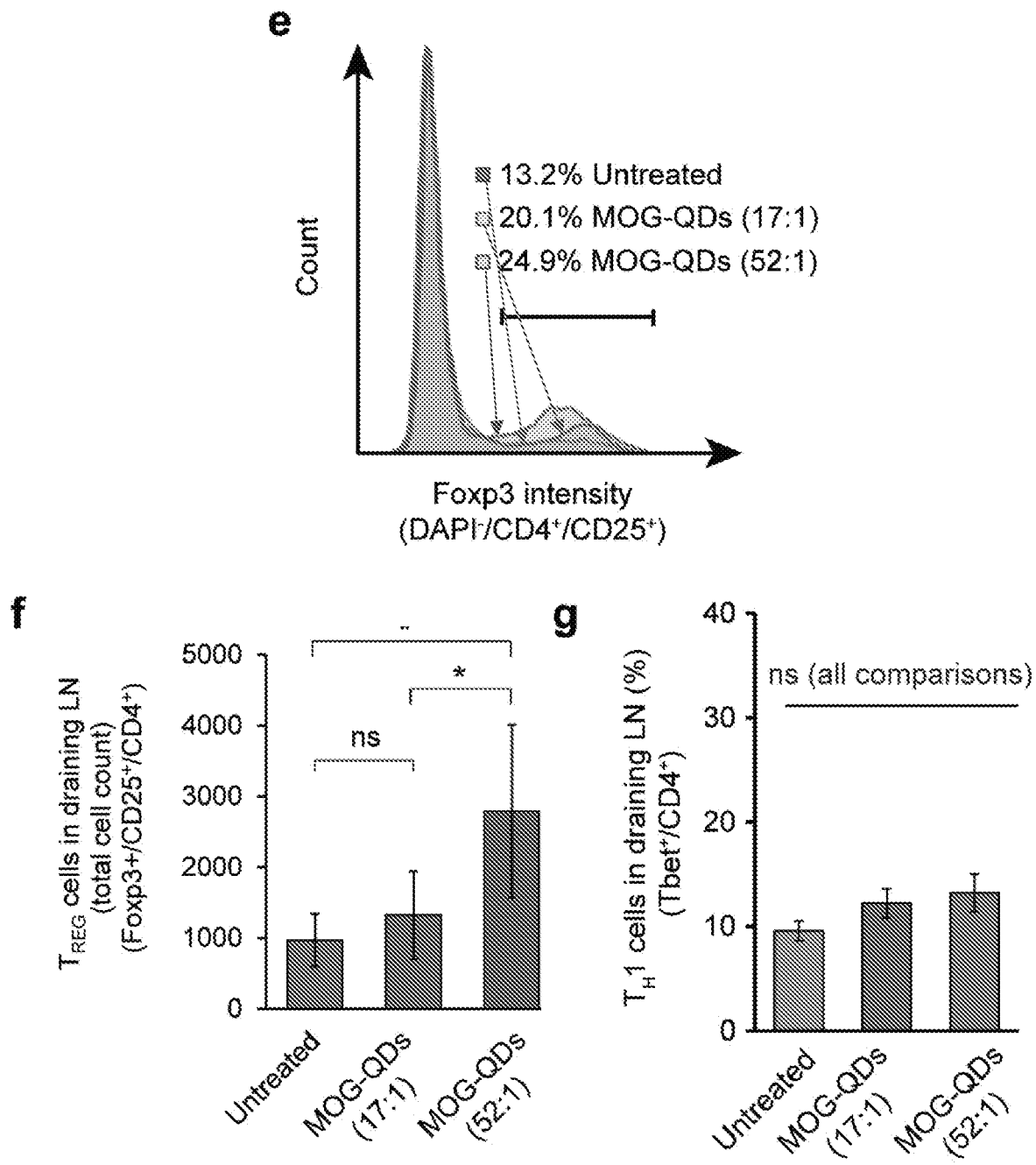
Figure 17:
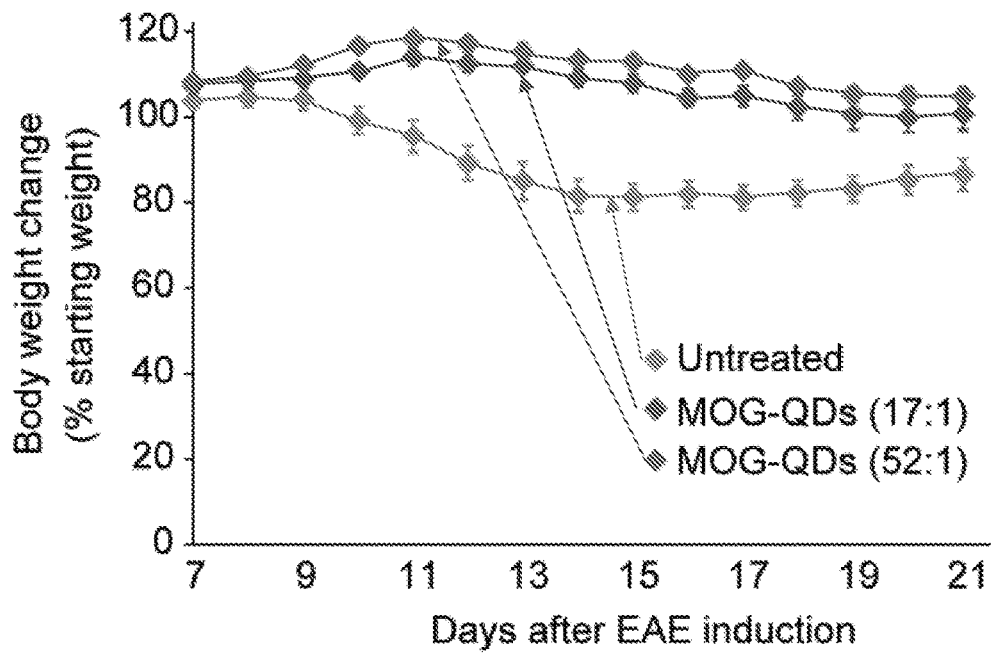
FIG. 17 shows body weight change was measured daily as an indicator of disease severity for mice receiving MOG-QDs treatments of 17:1 or 52:1.

This Example demonstrates that MOG-QD control disease in a dose-dependent manner. In particular analyzed the role of MOG dose on the extent of tolerance induced by MOG-QD treatment. Mice were again induced with EAE and received an injection of MOG-QDs on day 2 (FIG. 5a). While the mass of QD was fixed in these studies, two different MOG ligand densities, 17:1 and 52:1 (MOG:QD), were displayed on these QD, altering the dose of MOG while keeping the number of QDs constant. Compared with untreated mice, both MOG-QD treatments conferred therapeutic effects. Interestingly, the higher dose nearly eliminated disease-induced paralysis, as indicated by a markedly lower clinical score (FIG. 5b), while the lower dose caused a significant, but lesser therapeutic effect. Relative to this lower dose, the higher MOG dose conferred efficacy that was statistically significant at several points during peak disease (e.g., day 17, day 19). The higher MOG dose (MOG-QD 52:1) also drove a 10-fold reduction in disease incidence—1 out of 10 mice—compared to 100% incidence in untreated mice, and 40% incidence in mice treated with the lower MOG dose (MOG-QD 17:1) (FIG. 5c). Compared to untreated mice, the incidences at the end of the study were significantly lower for both the 17:1 ($p<0.01$) and 52:1 treatments ($p<0.0001$). At the peak of disease (day 17), untreated mice exhibited a mean clinical score of 3.0 (complete hind limb paralysis), while mice treated with QD formulations exhibited mean scores of 1.0 (loss of tail function) and 0.5 (limp tip of tail), for the low and high ligand densities, respectively (FIG. 5d). MOG-QD treatment also significantly reduced weight loss (FIG. 17).

Example 6

Figure 18:
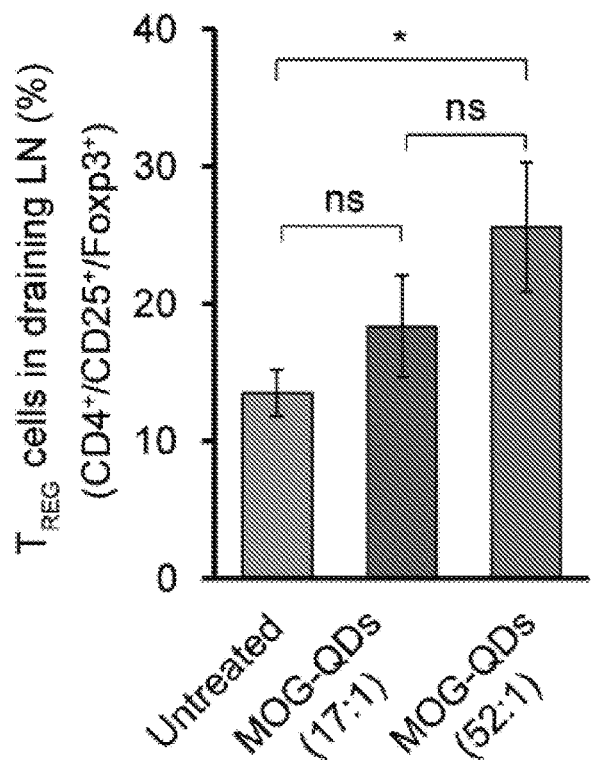
FIG. 18 shows the percentage of $T_{REG}$ cells in the draining LN was measured by flow cytometry as Foxp3$^+$ of CD25$^+$ of CD4$^+$ T cells.

This Example demonstrates that MOG-QD expand regulatory T cells without increasing inflammatory $T_H1$ cells. We analyzed whether efficacy in controlling disease results from MOG-QD driven expansion of $T_{REGS}$ (CD4$^+$/CD25$^+$/Foxp3$^+$). Thus mice with EAE were treated with MOG-QDs (17:1 or 52:1) on day 2 as in FIG. 5a, then iLNs were harvested and analyzed by flow cytometry on day 9. MOG-QDs significantly expanded the number of $T_{REGS}$ at the higher density, and caused an upward trend at the lower density (FIG. 5e,f). Similar results were measured in the frequency of $T_{REGS}$ (FIG. 18). Since uncontrolled delivery of myelin peptides during autoimmunity could exacerbate disease,[5] we sought to confirm MOG-QDs do not expand inflammatory $T_H1$ cells (i.e., Tbet$^+$ among CD4$^+$ T cells). These studies revealed no significant increases in $T_H1$ populations between treated and untreated groups (FIG. 5g).

Example 7

Figure 6:
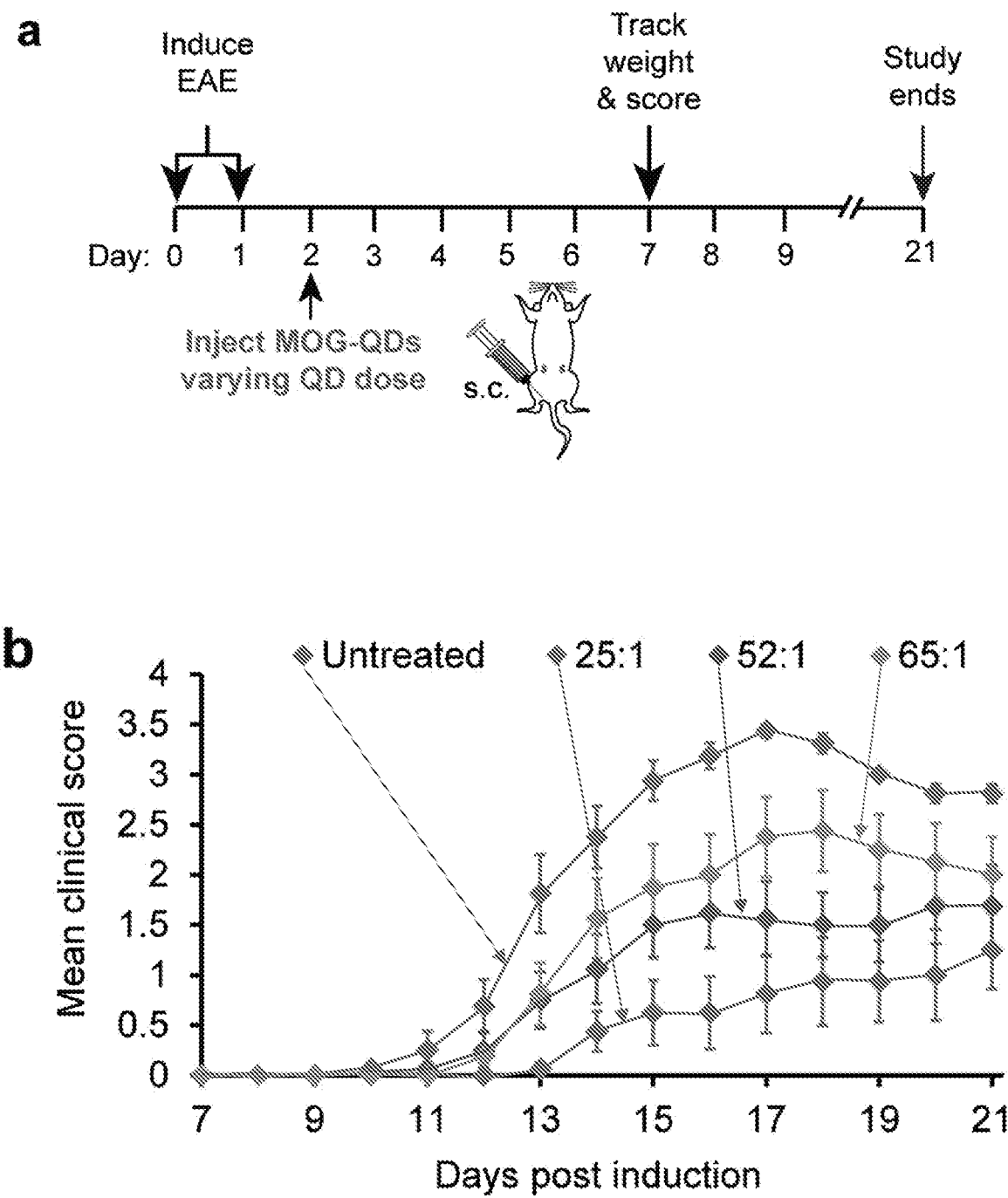
FIG. 6 shows tolerance is dependent on MOG ligand density. Mice were induced with EAE on days 0 and 1, followed by treatment with MOG-QDs of varying QD dose on day 2 (a). Disease progression was again monitored by clinical score (b) and peak disease was compared at day 17 (c). Disease incidence was assessed by onset of symptoms (d) and body weight loss was tracked through day 21 (e). Data in b-e represent the mean (N=5)±s.e.m. Statistical significance for c was determined by one-way ANOVA with post-test corrections for multiple comparisons and log-rank tests were used in d. For all tests, p values ≤0.05 were considered significant (*$p<0.05$, **$p<0.01$).
Figure 6:
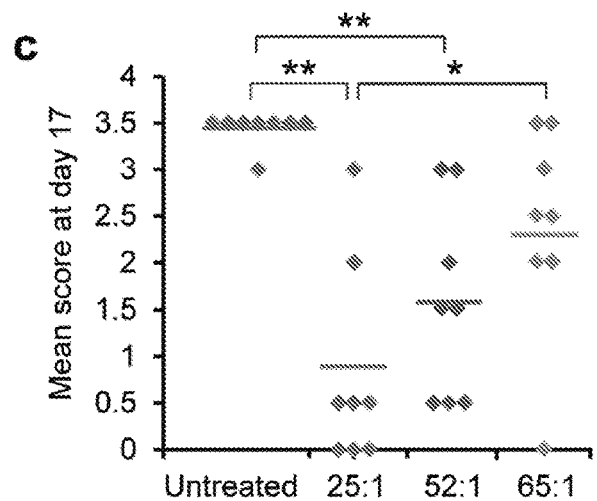
Figure 6:
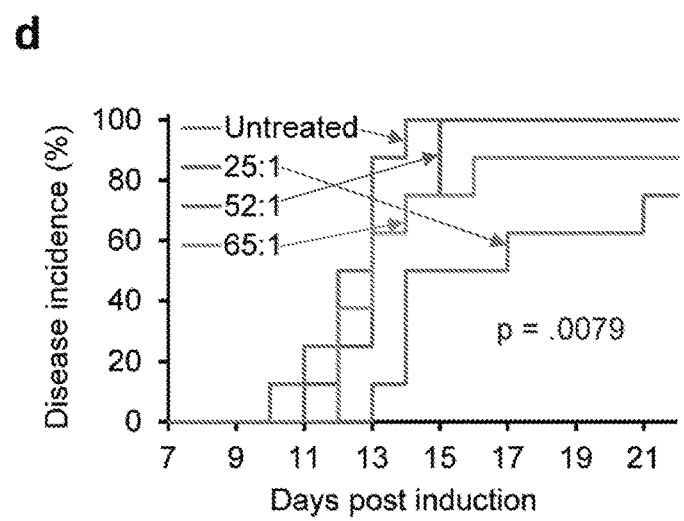
Figure 6:
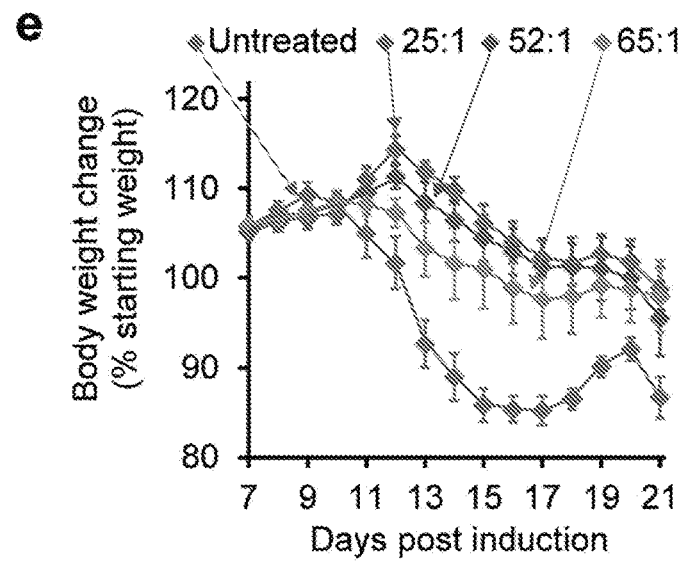

This Example demonstrates that tolerance and efficacy during EAE correlates inversely with peptide display density. To directly investigate the role of ligand density, we prepared MOG-QDs at three ligand densities, then injected groups of mice with EAE using constant masses of MOG, but displaying these doses on different numbers of QDs (i.e., fixed dose of MOG, varying number of QDs) (FIG. 6a). Intriguingly, over the course of the study, mice receiving a 25:1 MOG:QD dose (i.e., the fewest number of peptides per QD) exhibited the lowest clinical scores, with scores increasingly in order for 52:1 and 65:1 (i.e., the greatest number of peptides per QD) (FIG. 6b). These differences were statistically significant at several points, including the peak of disease (day 17). At this time, mice receiving 25:1 MOG:QDs exhibited a mean score 3-fold lower than mice treated with 65:1 MOG:QDs (FIG. 6c). Additionally, mice injected with the lowest ligand density of MOG:QDs showed both delayed disease onset and lower incidence compared with all other groups (FIG. 6d). An additional indicator of EAE severity is body weight loss. For this metric, a similar trend to that measured for clinical score was observed, where mice treated with 25:1 MOG:QDs maintained the highest percentage of original body weight, and weight loss increased as the number of MOG peptides per QD increased (FIG. 6e).

Because most therapies for MS and other autoimmune diseases are broadly suppressive, there is intense research to generating more selective therapies. The immune system offers this potential, and the control biomaterials could provide toward this goal has spurred great interest at this interface. This disclosure adds a fundamental discovery to the field: that a higher number of tolerogenic particles displaying lower levels of self-peptide is more effective for inducing tolerance than fewer particles displaying high densities of peptide. This indicates that a large number of low-density/dose events may lead to more effective control of autoimmune or inflammatory reactions then larger doses distributed among fewer particles or carriers.

Example 8

This Example provides a description of the materials and methods used to obtain the results descried above, and as represented in the figures.

Materials:

MOG modified for attachment to QDs (HHHHH-SAAAAAGMEVGWYRSPFSRVVHLYRNGK (SEQ ID NO: 3), denoted "MOG" in the text) and a similarly-modified control peptide from ovalbumin (HHHHH-SAAAAAGISQAVHAAHAEINEAGR; denoted "CTRL" in text (SEQ ID NO: 6)) were synthesized by Genscript (Piscataway, N.J.). Molecular Biology Grade Water and RPMI-1640 media were purchased from Lonza (Allendale, N.J.). Fetal bovine serum (FBS) was supplied by Corning (Tewksbury, Mass.). 2-Mercaptoethanol and Amicon Ultra Centrifugal Filters were purchased from Sigma Aldrich (St. Louis, Mo.). HEPES, non-essential amino acids, and 40 µm cell strainers were purchased from VWR (Radnor, Pa.). OPC oligonucleotide purification cartridges, L-Glutamine, Penicillin-Streptomycin, and 4',6-diamidino-2-phenylindole (DAPI) were purchased from Thermo Fisher Scientific (Grand Island, N.Y.). Spleen Dissociation Medium and CD4 negative selection kits were from STEMCELL Technologies (Vancouver, British Columbia, Canada). CD11c microbeads were purchased from Miltenyi Biotec (Cambridge, Mass.). CpG adjuvant (5'-TCC ATG ACG TTC CTG ACG TT-3', (SEQ ID NO: 7)) was synthesized by IDT (Coralville, Iowa). Fluorescent antibody conjugates for flow cytometry were purchased from BD (San Jose, Calif.). eFlour 670 proliferation dye was supplied by affymetrix eBioscience (San Diego, Calif.). FITC CD45R/B220 (BD), CD3e (abcam, Cambridge, Mass.), DL405 IgG (Jackson Immunoresearch, West Grove, Pa.), F4/80 (BD), Biotinylated MARCO (R&D Systems, Minneapolis, Minn.), and Streptavadin Alexa 488 (Jackson Immunoresearch) were used for immunohistochemical staining of iLN sections. EAE induction kits were supplied by Hooke Laboratories (Lawrence, Mass.).

Cells and Animals:

All primary cells were harvested from female C57BL/6 mice (4-12 weeks, stock #000664) and male C57BL/6-Tg (Tcra2D2,Tcrb2D2)1Kuch/J (2D2) mice (10-16 weeks, stock #006912) purchased from Jackson Laboratories (Bar Harbor, Me.). 2D2 mice display transgenic CD4$^+$ T cell receptors specific for MOG residues 35-55. Mice induced with EAE were female C57BL/6 mice (10-12 weeks, stock #000664). All animals were cared for in compliance with Federal, State, and local guidelines, and using protocols reviewed and approved by the University of Maryland's Institutional Animal Care and Use Committee (IACUC).

Characterization of Quantum Dots and Peptide-QD Assemblies:

The 625 nm emitting QDs and their cap-exchange with CL4 ligands have been previously described.[41] Peptides were desalted prior to QD conjugation as described.[42] MOG peptide has a net charge of +4 at pH 7. MOG and CTRL were assembled on QDs by mixing solutions of desalted peptide in molecular biology grade water with QDs at defined molar ratios. TEM, gel electrophoresis, and DLS analysis were performed as described.[41]

Quantification of Peptide Loading on QDs:

We utilized an established fluorescence method to verify peptide binding to QDs by the same mechanism.[43] A Cy3-labeled peptide terminating in a (His)$_6$ (SEQ ID NO: 8) motif was self-assembled to the QDs across a range of ratios including 0, 10, 25, 50, 75, 100, 125, and 150 peptides/QD in 100 μL of PBS. Equal amounts of free dye-labeled peptide without QD were added to the same volume of PBS as controls. Following self-assembly, all samples were loaded into 0.5 mL Amicon Ultra Centrifugal Filters with a 50,000 NMWL and centrifuged at 14,000×g for 10 min. The amount of free dye-labeled peptide from the QD samples was then compared to that from the unbound dye-labeled peptide only control samples using UV absorbance.

Simulation of MOG-QD Peptide Assembly:

The MOG-QD peptide assembly was simulated in silico in a manner similar to that we described previously for other peptides.[31, 32, 44-46] These structures and calculations were prepared using Chimera and Chem-3D Ultra 11.0. Energy was minimized using the MM2 module and the most probable conformation when attached to the QD were selected. A hard sphere was used to represent the quantum dot (QD) core/shell structure, which was covered with the surface-functionalizing ligand at an extension estimated from dynamic light scattering (DLS) measurements and energy minimization. The core MOG peptide structure was taken directly from the crystallographic structure 1PKO in the Protein Data Bank.[47] The remaining (His)$_5$S(Ala)$_5$G (SEQ ID NO: 2) N-terminal portion was docked to the QD surface via the (His)$_5$ (SEQ ID NO: 3) sequence with the (Ala)$_5$G (SEQ ID NO: 9) portion in an energy-minimized alpha helical conformation. Probabilities for peptide ligand density distributions were calculated using a Poisson distribution as previously described and confirmed experimentally.[48]

Dendritic Cell Isolation and Flow Cytometry:

CD11c$^+$ dendritic cells (DCs) were isolated from the spleens of female C57BL/6 mice through positive selection with Spleen Dissociation Media (STEMCELL) and CD11c Microbeads (Miltenyi). DC purities after isolation varied slightly across experiments, but were 90% or greater. DCs were plated in a 96 well plate at 100,000 cells per well and cultured in RPMI 1640 media supplemented with 10% FBS, 2 mM L-glutamine, 1× non-essential amino acids, 10 mM HEPES buffer, 1× penicillin and streptomycin, and 55 μM β-mercaptoethanol at 37° C. and 5% $CO_2$. For uptake studies, DCs were incubated with 150:1 MOG-QDs for 2 hours, stained with DAPI, and examined by flow cytometry (BD Cantoll, San Jose, Calif.) for presence of MOG-QDs and viability. Viability was determined by cells staining negative for DAPI. Data were analyzed with FlowJo v.10 (TreeStar, Ashland, Oreg.).

DC Activation, T Cell Co-Culture, and Flow Cytometry:

Isolated DCs were treated with CpG to induce the expression of costimulatory factors and either MOG or CTRL in soluble or QD-conjugated form and cultured for 24 hours. DC activation was then analyzed by staining for CD40, CD80, and CD85 markers. Stained cells were analyzed by flow cytometry. CD4$^+$ T cells were then isolated from the spleens of 2D2 mice via a negative selection kit (STEMCELL) and labelled with eFlour 670 proliferation dye. 300,000 T cells were then added to the wells containing treated DCs. After 72 hours, cell viability was assessed by DAPI staining and T cell proliferation was analyzed by a decrease in fluorescent signal as dye is diluted in daughter cells during successive generations. Cells in all in vitro studies were treated with a dose of QDs ranging from 0.44 to 40 picomoles and a dose of MOG ranging from 0.25 to 10 μg.

Analysis of QD Drainage in Mice:

Mice were injected with MOG-QDs and 24 hours later, the draining and non-draining iLNs were harvested for analysis. LNs were passed through a 40 μm strainer to create a single cell suspension. Cells were then stained with DAPI and analyzed by flow cytometry for viability (i.e., DAPI$^-$) and presence of fluorescent MOG-QDs. Additional iLNs were frozen, sectioned, and fixed for staining. In one analysis, sections were stained for T cells (CD3e) and B cells (B220). In an additional study, sections were stained with antibodies for macrophages (F4/80) and the scavenger receptor MARCO. iLN sections were visualized by fluorescent microscopy (Olympus IX-83) for presence of MOG-QDs, T cells, B cells, macrophages, and MARCO. ImageJ was used for image processing and analysis. All images in a particular study were analyzed in an identical manner that was applied to the entire image area.

EAE Induction and Monitoring:

C57BL/6 mice (female, 10-12 weeks) were induced with EAE following a defined protocol from Hooke Labs. Briefly, mice were injected s.c. with an emulsion of MOG and complete Freund's adjuvant (CFA) at the upper and lower back on day 0. Pertussis toxin was also administered intraperitoneally 2 and 24 hours after MOG/CFA injection. Beginning at day 7, mice were weighed to detect changes from day 0 body weight (a symptom of disease) and scored for disease severity with respect to paralysis. A standard clinical scoring rubric was used: 0—no symptoms, 1—limp tail, 2—weakness of hind legs, 3—hind limb paralysis, 4—hind limb paralysis and partial front limb paralysis, 5—moribund.[6, 7, 15] Disease incidence was defined as the first day a mouse displayed symptoms of paralysis.

MOG-QD Treatment:

Mice induced with EAE were randomly divided into groups of 8-10 mice each. A control group was left untreated in each experiment. In one experiment, additional groups were treated by s.c. injection at the tailbase with 0.2 nanomoles QDs, 70 μg MOG, 70 μg CTRL peptide on 0.2 nanomoles QDs (100:1), or 70 μg MOG peptide on 0.2 nanomoles QDs (100:1). Similar experiments contained two treatment groups: 14.3 μg MOG on 0.4 nanomoles QDs (17:1) or 73 μg MOG on 0.2 nanomoles QDs (52:1). The final experiment design contained three treatment groups: 70

µg MOG on 0.5 nanomoles QDs (25:1), 70 µg MOG on 0.4 nanomoles QDs (52:1), or 70 µg MOG on 0.3 nanomoles QDs (65:1).

EAE T Cell Readout:

Mice were induced with EAE and treated with MOG-QDs as described above. On day 9, the iLNs were removed for analysis by flow cytometry. iLNs were mashed through a 40 µm strainer to create a single cell suspension and stained for T cell surface markers ($CD4^+$, $CD25^+$) and transcription factors ($Tbet^+$, $Foxp3^+$). Tbet and Foxp3 are common transcription factors used to identify $T_H1$ and $T_{REG}$, respectively. Cells were examined with flow cytometry and data were again analyzed with FlowJo v.10.

Statistics:

One-way ANOVA with a Tukey post-test was used to compare three or more groups for in vitro studies and overall disease metrics from in vivo studies. For in vivo studies, two-way ANOVA was used to compare three groups monitored over time, with post-test corrections for multiple comparisons. Log-rank tests were used in analysis of disease incidence. For all tests, p values ≤0.05 were considered significant. For all figures, $*p<0.05$, $p<0.01$, $*p<0.001$, $****p<0.0001$, $^{\#}p<0.05$.

It will be recognized from the foregoing that QDs modified with myelin or control peptides exhibited tunable, uniform features—peptide display density and size, for example. These materials were non-toxic to primary immune cells and did not trigger any intrinsic inflammatory responses. In mice, the peptide-QDs rapidly drained to lymph nodes following injection, and were co-localized with macrophages expressing scavenger receptors involved in tolerance. MOG-QD treatment in mice induced with a mouse model of MS drastically reduced disease severity and incidence, while QDs modified with control peptide sequences did not. These therapeutic effects were tunable and directly correlated with not just the dose, but with the density of MOG ligands assembled on the QD surfaces.

REFERENCES

[1] H. F. McFarland, R. Martin, *Nat. Immunol.* 2007, 8, 913.
[2] M. Comabella, S. J. Khoury, *Clin. Immunol.* 2012, 142, 2.
[3] J. A. Bluestone, H. Bour-Jordan, M. Cheng, M. Anderson, *J. Clin. Invest.* 2015, 125, 2250.
[4] F. Piehl, *J. Intern. Med.* 2014, 275, 364.
[5] A. Lutterotti, R. Martin, *Expert Opin. Investig. Drugs* 2014, 23, 9.
[6] J. M. Gammon, L. H. Tostanoski, A. R. Adapa, Y.-C. Chiu, C. M. Jewell, *J. Controlled Release* 2015, 210, 169.
[7] X. Clemente-Casares, J. Blanco, P. Ambalavanan, J. Yamanouchi, S. Singha, C. Fandos, S. Tsai, J. Wang, N. Garabatos, C. Izquierdo, S. Agrawal, M. B. Keough, V. W. Yong, E. James, A. Moore, Y. Yang, T. Stratmann, P. Serra, P. Santamaria, *Nature* 2016, 530, 434.
[8] L. H. Tostanoski, E. A. Gosselin, C. M. Jewell, *Discov. Med.* 2016, 21, 403.
[9] I. K. Gratz, M. D. Rosenblum, M. M. Maurano, J. S. Paw, H. A. Truong, A. Marshak-Rothstein, A. K. Abbas, *J. Immunol.* 2014, 192, 1351.
[10] L. H. Tostanoski, Y. C. Chiu, J. I. Andorko, M. Guo, X. Zeng, P. Zhang, W. Royal, 3rd, C. M. Jewell, *ACS Nano* 2016,
[11] K. L. Hess, J. I. Andorko, L. H. Tostanoski, C. M. Jewell, *Biomaterials* 2016, 118, 51.
[12] P. Zhang, Y. C. Chiu, L. H. Tostanoski, C. M. Jewell, *ACS Nano* 2015, 9, 6465.
[13] M. A. Swartz, J. A. Hubbell, S. T. Reddy, *Semin. Immunol.* 2008, 20, 147.
[14] S. T. Reddy, A. J. van der Vlies, E. Simeoni, V. Angeli, G. J. Randolph, C. P. O'Neil, L. K. Lee, M. A. Swartz, J. A. Hubbell, *Nat. Biotechnol.* 2007, 25, 1159.
[15] D. R. Getts, A. J. Martin, D. P. McCarthy, R. L. Terry, Z. N. Hunter, W. T. Yap, M. T. Getts, M. Pleiss, X. Luo, N. J. King, L. D. Shea, S. D. Miller, *Nat. Biotechnol.* 2012, 30, 1217.
[16] D. R. Getts, R. L. Terry, M. T. Getts, C. Deffrasnes, M. Muller, C. van Vreden, T. M. Ashhurst, B. Chami, D. McCarthy, H. Wu, J. Ma, A. Martin, L. D. Shae, P. Witting, G. S. Kansas, J. Kuhn, W. Hafezi, I. L. Campbell, D. Reilly, J. Say, L. Brown, M. Y. White, S. J. Cordwell, S. J. Chadban, E. B. Thorp, S. Bao, S. D. Miller, N. J. King, *Sci. Transl. Med.* 2014, 6, 219ra7.
[17] S. Kontos, I. C. Kourtis, K. Y. Dane, J. A. Hubbell, *Proc. Natl. Acad. Sci. U.S.A.* 2013, 110, E60.
[18] L. H. Tostanoski, Y. C. Chiu, J. M. Gammon, T. Simon, J. I. Andorko, J. S. Bromberg, C. M. Jewell, *Cell Rep.* 2016, 16, 2940.
[19] A. Louveau, I. Smirnov, T. J. Keyes, J. D. Eccles, S. J. Rouhani, J. D. Peske, N. C. Derecki, D. Castle, J. W. Mandell, K. S. Lee, T. H. Harris, J. Kipnis, *Nature* 2015, 523, 337.
[20] A. Aspelund, S. Antila, S. T. Proulx, T. V. Karlsen, S. Karaman, M. Detmar, H. Wiig, K. Alitalo, *J. Exp. Med.* 2015, 212, 991.
[21] C. E. Probst, P. Zrazhevskiy, V. Bagalkot, X. Gao, *Adv. Drug. Deliv. Rev.* 2013, 65, 703.
[22] W. R. Algar, K. Susumu, J. B. Delehanty, I. L. Medintz, *Anal. Chem.* 2011, 83, 8826.
[23] S. J. Rosenthal, J. C. Chang, O. Kovtun, J. R. McBride, I. D. Tomlinson, *Chem. Biol.* 2011, 18, 10.
[24] B. K. Andrasfalvy, G. L. Galinanes, D. Huber, M. Barbic, J. J. Macklin, K. Susumu, J. B. Delehanty, A. L. Huston, J. K. Makara, I. L. Medintz, *Nat. Methods* 2014, 11, 1237.
[25] J. B. Blanco-Canosa, M. Wu, K. Susumu, E. Petryayeva, T. L. Jennings, P. E. Dawson, W. R. Algar, I. L. Medintz, *Coord. Chem. Rev.* 2014, 263-264, 101.
[26] K. Boeneman, J. B. Delehanty, J. B. Blanco-Canosa, K. Susumu, M. H. Stewart, E. Oh, A. L. Huston, G. Dawson, S. Ingale, R. Walters, M. Domowicz, J. R. Deschamps, W. R. Algar, S. DiMaggio, J. Manono, C. M. Spillmann, D. Thompson, T. L. Jennings, P. E. Dawson, I. L. Medintz, *ACS Nano* 2013, 7, 3778.
[27] R. Agarwal, M. S. Domowicz, N. B. Schwartz, J. Henry, I. Medintz, J. B. Delehanty, M. H. Stewart, K. Susumu, A. L. Huston, J. R. Deschamps, P. E. Dawson, V. Palomo, G. Dawson, *ACS Chem. Neurosci.* 2015, 6, 494.
[28] T. S. Hauck, R. E. Anderson, H. C. Fischer, S. Newbigging, W. C. Chan, *Small* 2010, 6, 138.
[29] L. Ye, K. T. Yong, L. Liu, I. Roy, R. Hu, J. Zhu, H. Cai, W. C. Law, J. Liu, K. Wang, J. Liu, Y. Liu, Y. Hu, X. Zhang, M. T. Swihart, P. N. Prasad, *Nat. Nanotechnol.* 2012, 7, 453.
[30] S. Kim, Y. T. Lim, E. G. Soltesz, A. M. De Grand, J. Lee, A. Nakayama, J. A. Parker, T. Mihaljevic, R. G. Laurence, D. M. Dor, L. H. Cohn, M. G. Bawendi, J. V. Frangioni, *Nat. Biotechnol.* 2004, 22, 93.
[31] D. E. Prasuhn, J. R. Deschamps, K. Susumu, M. H. Stewart, K. Boeneman, J. B. Blanco-Canosa, P. E. Dawson, I. L. Medintz, *Small* 2010, 6, 555.
[32] I. L. Medintz, A. R. Clapp, F. M. Brunel, T. Tiefenbrunn, H. Tetsuo Uyeda, E. L. Chang, J. R. Deschamps, P. E. Dawson, H. Mattoussi, *Nat. Mater.* 2006, 5, 581.

[33] I. L. Medintz, J. H. Konnert, A. R. Clapp, I. Stanish, M. E. Twigg, H. Mattoussi, J. M. Mauro, J. R. Deschamps, *Proc. Natl. Acad. Sci. U.S.A.* 2004, 101, 9612.
[34] W. R. Algar, A. Malonoski, J. R. Deschamps, J. B. Blanco-Canosa, K. Susumu, M. H. Stewart, B. J. Johnson, P. E. Dawson, I. L. Medintz, *Nano Lett.* 2012, 12, 3793.
[35] W. R. Algar, M. G. Ancona, A. P. Malanoski, K. Susumu, I. L. Medintz, *ACS Nano* 2012, 6, 11044.
[36] J. I. Andorko, K. L. Hess, C. M. Jewell, *AAPSI* 2015, 17, 323.
[37] K. J. Warren, D. Iwami, D. G. Harris, J. S. Bromberg, B. E. Burrell, *J. Clin. Invest.* 2014, 124, 2204.
[38] M. S. Arredouani, F. Franco, A. Imrich, A. Fedulov, X. Lu, D. Perkins, R. Soininen, K. Tryggvason, S. D. Shapiro, L. Kobzik, *J. Immunol.* 2007, 178, 5912.
[39] T. Korn, J. Reddy, W. Gao, E. Bettelli, A. Awasthi, T. R. Petersen, B. T. Backstrom, R. A. Sobel, K. W. Wucherpfennig, T. B. Strom, M. Oukka, V. K. Kuchroo, *Nat. Med.* 2007, 13, 423.
[40] S. L. Bailey, B. Schreiner, E. J. McMahon, S. D. Miller, *Nat Immunol* 2007, 8, 172.
[41] K. Susumu, E. Oh, J. B. Delehanty, J. B. Blanco-Canosa, B. J. Johnson, V. Jain, W. J. Hervey, W. R. Algar, K. Boeneman, P. E. Dawson, I. L. Medintz, *J. Am. Chem. Soc.* 2011, 133, 9480.
[42] K. E. Sapsford, D. Farrell, S. Sun, A. Rasooly, H. Mattoussi, I. L. Medintz, *Sensors and Actuators B: Chemical* 2009, 139, 13.
[43] I. L. Medintz, A. R. Clapp, H. Mattoussi, E. R. Goldman, B. Fisher, J. M. Mauro, *Nat. Mater.* 2003, 2, 630.
[44] K. Boeneman, J. R. Deschamps, S. Buckhout-White, D. E. Prasuhn, J. B. Blanco-Canosa, P. E. Dawson, M. H. Stewart, K. Susumu, E. R. Goldman, M. Ancona, I. L. Medintz, *ACS Nano* 2010, 4, 7253.
[45] I. L. Medintz, T. Pons, K. Susumu, K. Boeneman, A. Dennis, D. Farrell, J. R. Deschamps, J. S. Melinger, G. Bao, H. Mattoussi, *J. Phys. Chem. C Nanomater. Interfaces* 2009, 113, 18552.
[46] I. L. Medintz, K. E. Sapsford, A. R. Clapp, T. Pons, S. Higashiya, J. T. Welch, H. Mattoussi, *J. Phys. Chem. B* 2006, 110, 10683.
[47] C. Breithaupt, A. Schubart, H. Zander, A. Skerra, R. Huber, C. Linington, U. Jacob, *Proc. Natl. Acad. Sci. U.S.A.* 2003, 100, 9446.
[48] T. Pons, I. L. Medintz, X. Wang, D. S. English, H. Mattoussi, *J. Am. Chem. Soc.* 2006, 128, 15324.

Although the present disclosure has been described with respect to one or more particular embodiments and/or examples, it will be understood that other embodiments and/or examples of the present disclosure may be made without departing from the scope of the present disclosure.

What is claimed is:

1. A quantum dot (QD) comprising a CdSe/ZnS component, the QD having conjugated thereon a plurality of myelin peptide antigen molecules, the antigen molecules comprising HHHHHSAAAAAG (SEQ ID NO:2), wherein $(H)_5$ of SEQ ID NO:2 participates in Zn-coordination of the peptide antigen on the QD.

2. The QD of claim 1, wherein the size of the quantum dot having the myelin peptide antigen molecules thereon is from 14 to 22 nm.

3. The QD of claim 1, wherein the number of myelin peptide antigen molecules on the QD are from 15 to 65.

4. The QD of claim 1, wherein the number of myelin peptide antigen molecules on the QD are from 13 to 59.

5. The QD of claim 1, wherein the density of myelin peptide antigen molecules on the QD are less than or equal to 0.56 peptide antigen molecules per $nm^2$ of QD surface area.

6. The QD of claim 1, wherein S in SEQ ID NO:2 acts as a flexible hinge to display the peptide away from the QD surface, and wherein $(A)_5$ is an alpha-helical spacer.

7. A composition comprising a plurality of quantum dots (QDs) of claim 1.

8. The composition of claim 7, wherein the QDs comprise a ratio of myelin peptide antigen to QD of from 1:1 to 150:1.

9. The composition of claim 8, wherein at least 80% of the QDs in the plurality have a diameter of from 10-40 nm.

10. A method for promoting tolerance to a myelin antigen comprising administering to an individual in need thereof a composition of claim 7.

11. The method of claim 10, wherein subsequent to the administration regulatory T cells ($T_{REGS}$) in the individual are expanded relative to a control.

12. The method of claim 10, wherein subsequent to the administration regulatory inflammatory $T_H1$ cells in the individual are not expanded relative to a control.

13. The method of claim 10, wherein the QDs comprise a lowest density of myelin peptide antigens having 17±4 myelin peptide antigens per QD, and wherein the QDs comprise a highest density of myelin peptide antigens having 52±7 myelin peptide antigens per QD.

14. The method of claim 10, wherein a composition comprising the plurality of QDs is administered to an individual who has a condition that comprises an autoimmune response to myelin.

15. The method of claim 14, wherein the individual has multiple sclerosis, and wherein one or more symptoms of the MS in the individual are alleviated or inhibited from developing.

16. The method of claim 15, wherein the QDs comprise a ratio of myelin peptide antigen to QD of less than 150:1, and wherein alleviation or inhibition of development of the MS symptoms in the individual is greater than alleviation or inhibition of symptoms of the MS relative to a control value for administration of QDs comprising a ratio of myelin peptide antigen to QD of 150:1 or higher.

17. The method of claim 15, wherein the QDs comprise a ratio of myelin peptide antigen to QD of less than 65:1, and wherein alleviation or inhibition of development of the MS symptoms in the individual is greater than alleviation or inhibition of symptoms of the MS relative to a control value for administration of QDs comprising a ratio of myelin peptide antigen to QD of 65:1 or higher.

18. The method of claim 15, wherein subsequent to the administration $T_{REGS}$ in the individual are expanded relative to a control, and/or wherein subsequent to the administration regulatory inflammatory $T_H1$ cells in the individual are not expanded relative to a control.

19. The method of claim 17, wherein subsequent to the administration $T_{REGS}$ in the individual are expanded relative to a control, and/or wherein subsequent to the administration regulatory inflammatory $T_H1$ cells in the individual are not expanded relative to a control.

* * * * *